United States Patent [19]

Wuchinich et al.

[11] Patent Number: 4,922,902
[45] Date of Patent: May 8, 1990

[54] METHOD FOR REMOVING CELLULAR MATERIAL WITH ENDOSCOPIC ULTRASONIC ASPIRATOR

[75] Inventors: David G. Wuchinich, New York; Donald R. Krawitt, Rhinebeck; Robert Brendolan, Mamaroneck; Louis Katz, Flushing, all of N.Y.

[73] Assignee: Valleylab, Inc., Boulder, Colo.

[21] Appl. No.: 133,711

[22] Filed: Dec. 16, 1987

Related U.S. Application Data

[60] Division of Ser. No. 20,266, Feb. 27, 1987, Pat. No. 4,750,488, and a continuation of Ser. No. 865,240, May 19, 1986, Pat. No. 4,750,902, which is a continuation-in-part of Ser. No. 770,342, Aug. 23, 1985, abandoned.

[51] Int. Cl.$^5$ ............................................. A61B 17/00
[52] U.S. Cl. ...................................... 604/22; 604/27; 606/168
[58] Field of Search .................... 128/24 A, 32, 303 R, 128/305, 328; 604/22, 27, 43

[56] References Cited

U.S. PATENT DOCUMENTS

| Re. 30,536 | 3/1981 | Perdreaux, Jr. ......................... 433/86 |
| 2,227,727 | 1/1941 | Leggiadro ............................ 128/319 |
| 2,514,080 | 7/1950 | Mason .................................. 171/327 |
| 2,714,890 | 8/1955 | Vang .................................... 128/305 |
| 2,723,386 | 11/1955 | Camp .................................... 340/111 |
| 2,845,072 | 7/1958 | Shafer ............................... 128/303.14 |
| 2,874,470 | 2/1954 | Richards ................................ 32/58 |
| 2,990,616 | 7/1961 | Balamuth et al. ....................... 32/26 |
| 3,027,690 | 4/1962 | Roney ..................................... 51/59 |
| 3,065,749 | 11/1962 | Brass ................................... 128/224 |
| 3,075,288 | 1/1963 | Balamuth et al. ....................... 32/58 |
| 3,076,904 | 2/1963 | Kleesattel et al. ..................... 310/26 |
| 3,086,288 | 4/1963 | Balamuth et al. ....................... 30/272 |
| 3,089,790 | 5/1963 | Balamuth et al. ....................... 134/1 |
| 3,109,426 | 11/1963 | Noonan et al. ....................... 128/240 |
| 3,113,225 | 12/1963 | Kleesattel ............................. 310/26 |
| 3,133,351 | 5/1964 | Von Seggern ........................... 32/26 |
| 3,149,633 | 9/1964 | Zingale ............................. 128/303.15 |
| 3,166,840 | 1/1965 | Bancroft et al. ....................... 29/470 |
| 3,213,537 | 10/1965 | Bulamuth et al. ........................ 32/28 |

(List continued on next page.)

FOREIGN PATENT DOCUMENTS

1429637 1/1966 France.
415949 6/1966 Switzerland.
790277 2/1958 United Kingdom.

OTHER PUBLICATIONS

Von Ardenne et al., "Ultrasonic Insertion of Small-Gauge Wire Probes and Hollow Needles in Living Organisms," 1960.
Watkins et al., "Ultrasound Detachment of Calcific Deposits from Diseased Cardiac Valve Specimens," 1960.
Acta Soc. Ophthalmol. Jap. 74 (8), pp. 733–738 (Aug. 1970).
Acta Soc. Ophthalmol. Jap. 74 (7), pp. 557–661 (Jul. 1970.
Acta Soc. Ophthalmol. Jap. 74 (6), pp. 497–503 (Jun. 1970).
Acta. Soc. Ophthalmol. Jap. 74 (10), pp. 1313–1327 (Oct. 1970).

(List continued on next page.)

Primary Examiner—Max Hindenburg
Assistant Examiner—Randy Citrin
Attorney, Agent, or Firm—Pennie & Edmonds

[57] ABSTRACT

A method and apparatus for endoscopic removal of compliant biological tissues utilizing an endoscopic ultrasonic aspirator comprising irrigation and aspiration means, a piezoelectric ultrasonic transducer, a first resonator such as a half-wave stepped velocity transformer, a probe including a second resonator such as a constant-stress velocity transformer, a blunt or modified working tip of open channel means or restricted tubular means for application of ultrasonic energy to cellular material, and a capacitive fluid sensor to detect the presence of irrigation fluid adjacent these transformers within the instrument. The surgery is advantageously performed by operating the transducer in the 10–20 kHz range to achieve maximum cavitation of the intracellular fluids in the tissues to be removed.

48 Claims, 14 Drawing Sheets

U.S. PATENT DOCUMENTS

| | | | |
|---|---|---|---|
| 3,368,280 | 2/1968 | Friedman et al. | 32/58 |
| 3,375,583 | 4/1968 | Blank et al. | 32/26 |
| 3,380,446 | 4/1968 | Martin | 128/24 |
| 3,433,226 | 3/1969 | Boyd | 128/305 |
| 3,526,219 | 9/1970 | Balamuth | 128/2 |
| 3,546,498 | 12/1970 | McMaster et al. | 310/8.2 |
| 3,565,062 | 2/1971 | Kuris | 128/24 |
| 3,589,363 | 6/1971 | Banko | 128/276 |
| 3,636,947 | 1/1972 | Balamath | 128/66 |
| 3,693,613 | 9/1972 | Kelman | 128/24 A |
| 3,805,787 | 4/1974 | Banko | 128/276 |
| 3,823,717 | 7/1974 | Pohlman et al. | 128/305 |
| 3,902,495 | 9/1975 | Weiss et al. | 128/276 |
| 3,941,122 | 3/1976 | Jones | 128/24 A |
| 3,956,826 | 5/1976 | Perdreaux, Jr. | 32/58 |
| 4,016,882 | 4/1977 | Broadwin et al. | 128/305 |
| 4,041,947 | 8/1977 | Weiss et al. | 128/276 |
| 4,063,557 | 12/1977 | Wuchinich et al. | 128/276 |
| 4,136,700 | 1/1979 | Broadwin | 128/305 |
| 4,146,019 | 3/1979 | Bass et al. | 128/6 |
| 4,223,676 | 9/1980 | Wuchinich et al. | 128/276 |
| 4,425,115 | 6/1984 | Wuchinich | 604/22 |
| 4,493,694 | 1/1985 | Wuchinich | 604/22 |
| 4,516,398 | 5/1985 | Wuchinich | 604/22 |
| 4,689,040 | 8/1987 | Thompson | 604/22 |

OTHER PUBLICATIONS

Acta. Soc. Ophthalmol. Jap. 73 (8), pp. 1165–1183 (Aug. 1969).
Karlin, Am. Jour. Opthal. 68 (1), Jul., 1969, pp. 84–91.
Acta. Soc. Ophthalmol. Jap. 74 (11), pp. 1484–1488 (Nov. 1970).
Acta. Soc. Ophthamol. Jap. 74 (8), pp. 725–732 (Aug. 1970).
Acta. Soc. Ophthamol. Jap. 74 (4), pp. 395–401 (Apr. 1970).
Endo–Urology Bulletin, (Richard Wolf) 1984.
Rely on Progress Bulletin (Richard Wolf) 1984.
Ultrasonic Surgery, Eighth Int'l Cong. Acous: London, 1974.
Personal Interview with Dr. C. D. Kelman (1970).
Vestnik Ophalmologia 82 (5), pp. 20–25 (1969).
Vestnik Ophalmologia (82) (5), pp. 26–28 (1969).
Frederick, Ultrasonic Engrg. pp. 66–130, 182–183, 308–363, J. Wiley, (1966).
Emery et al., "Phacoemulsification Aspiration of Cataracts", The C.V. Mosby Co., 1979, pp. xi and 5–7.
*Biomedical Ultrasonics*, P. N. T. Wells, London, 1977, pp. 57–58.
E. S. Flamm, et al., "Preliminary Experience with Ultrasnic Aspiration in Neurosurgery," *Neurosurgery*, vol. 2, No. 3, 1978, pp. 240–245.
W. Young et al., "Acute Physiological Effects of Ultrasonic Vibrations on Nervous Tissue," *Neurosurgery*, vol. 8, No. 6, 1981, pp. 689–694.
J. C. Addonizio et al., "Cavitron Ultrasonic Surgical Aspirator," *Urology*, vol. 23, No. 5, May, 1984, pp. 417–420.
R. T. Chopp, et al., "Use of Ultrasonic Surgical Aspirator in Renal Surgery," *Urology*, vol. 22, No. 2, Aug. 1983, pp. 157–159.
Isakovich et al., Sov. Phys.—accoust. 13 (4) Apr.–Jun. 1968, pp. 491–494.
Karlin, Ret. Detach. Surg., 73 Nov–Dec. 1969, pp. 1061–1076.
Kelman, Am. Jour. Ophthal, 64 (1), Jul. 1967, pp. 23–28.
Eisner et al., Ultrasonics, Apr.–Jun., 1965, pp. 88–98.
Kelman, Am. J. Ophthal. 69 (2) (1970), pp. 277–283.
Kelman et al., Am. J. Ophthal, 71 (6) (1971), pp. 1289–1291.

HIGH VELOCITY ULTRASONIC
EXTENSIONAL RESONATOR

STRESS DISTRIBUTIONS FOR VARIOUS
CROSS SECTION AREA VARIATIONS

VELOCITY DISTRIBUTIONS FOR
THE STRESS DISTRIBUTIONS OF FIG. 2

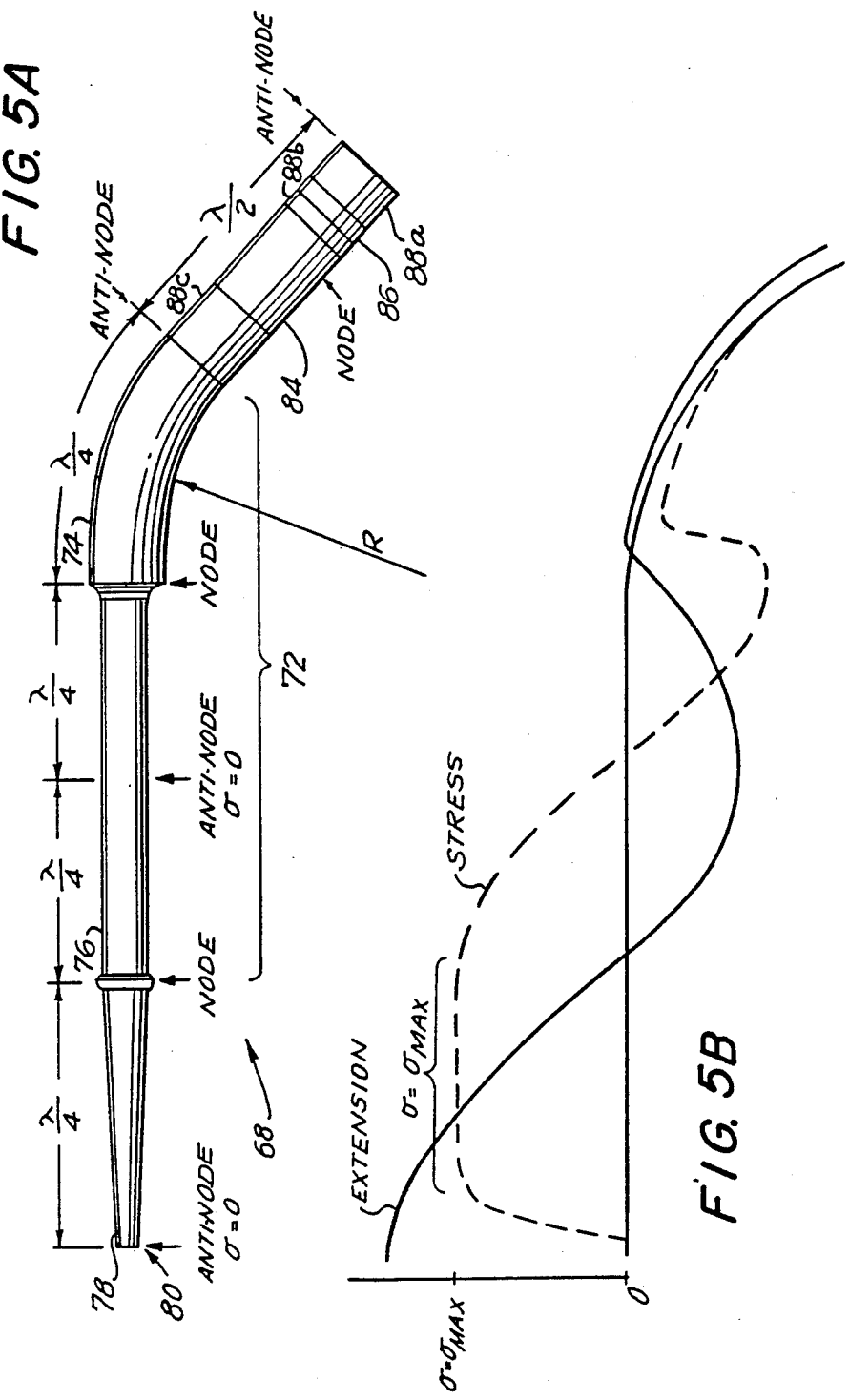

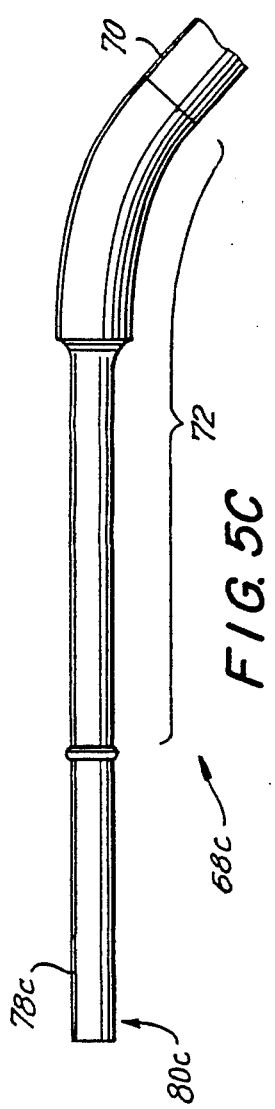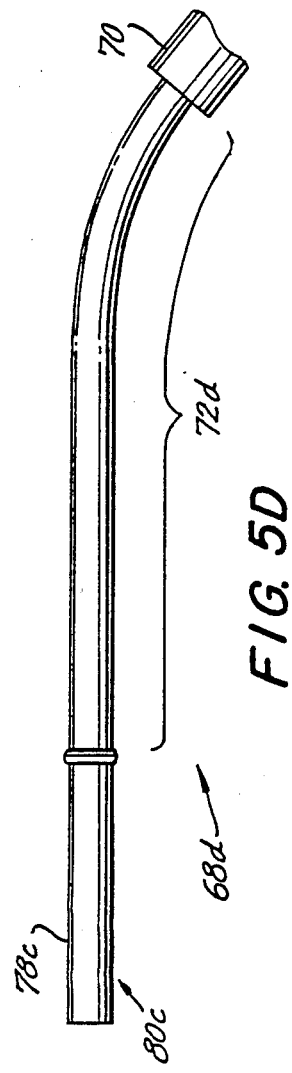

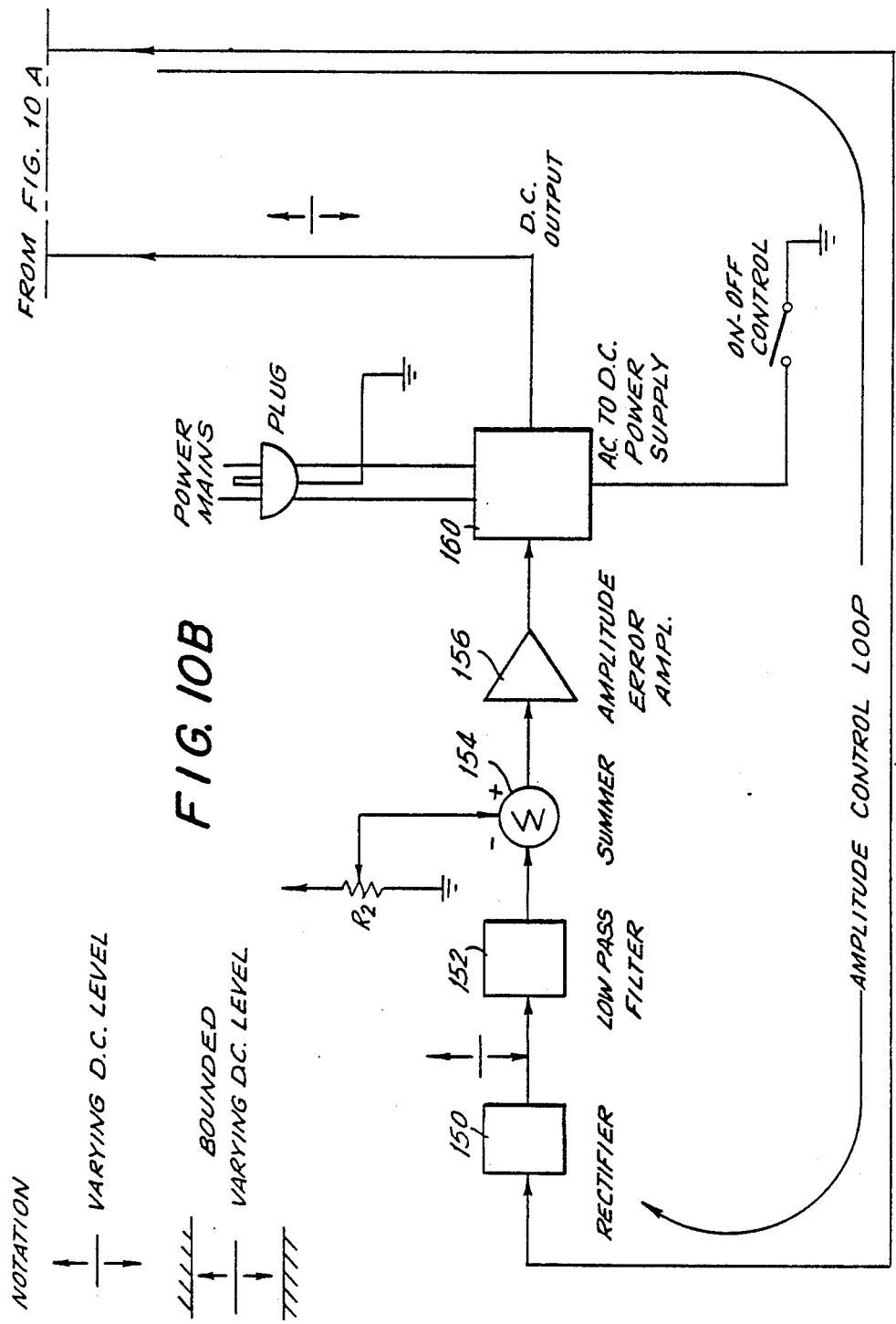

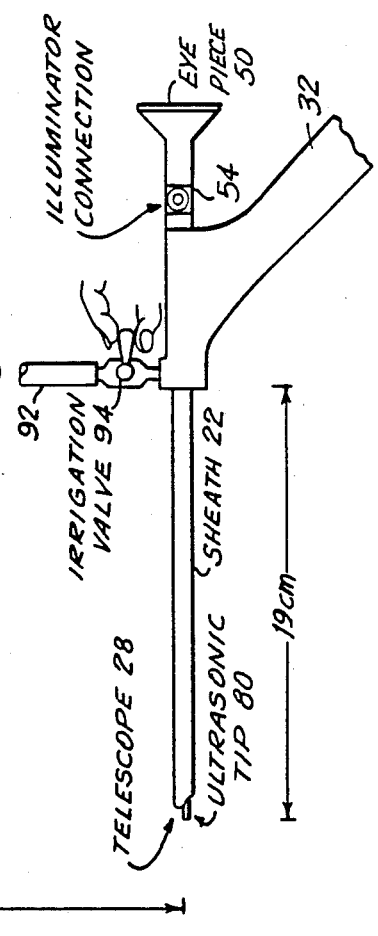
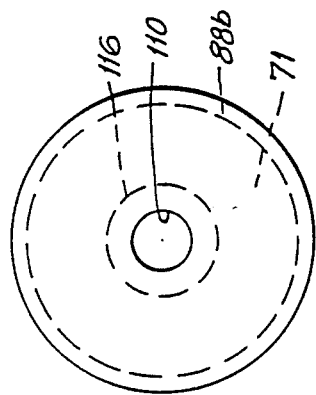

FIG. 14
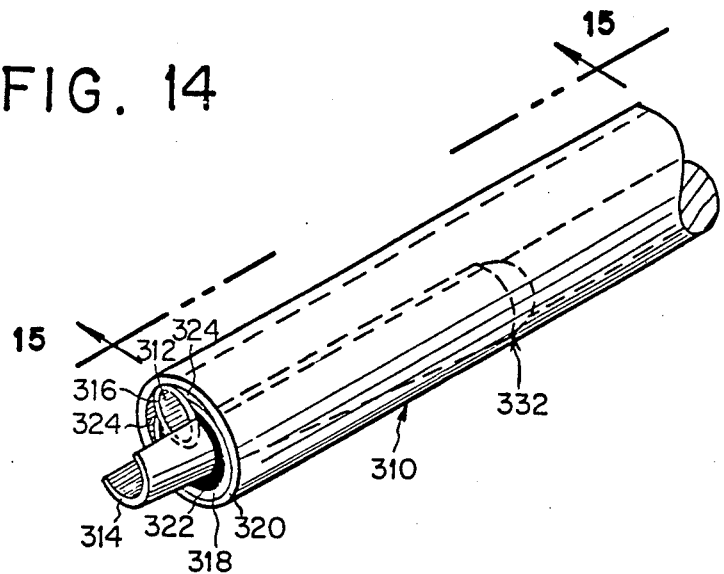
FIG. 15
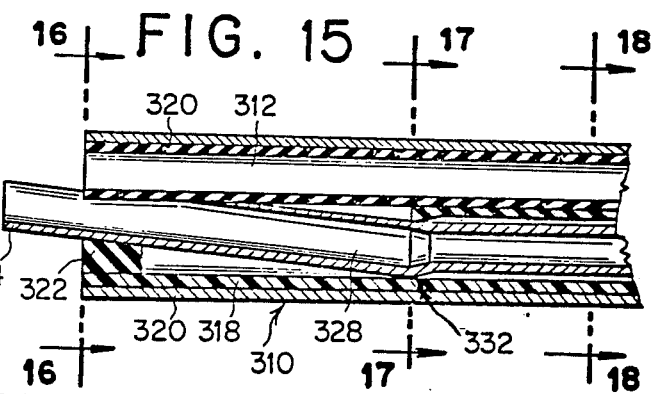
FIG. 16   FIG. 17   FIG. 18
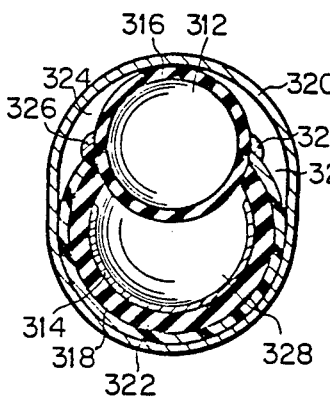 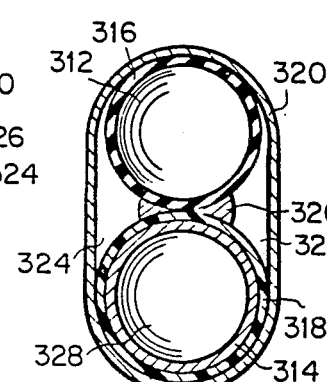 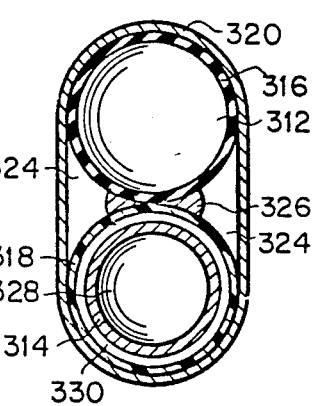

METHOD FOR REMOVING CELLULAR MATERIAL WITH ENDOSCOPIC ULTRASONIC ASPIRATOR

This application is a division of application Ser. No. 020,266, filed Feb. 27, 1987 now U.S. Pat. No. 4,750,488; and a continuation of application Ser. No. 865,240, filed May 19, 1986, now U.S. Pat. No. 4,750,902 which is a continuation-in-part of application Ser. No. 770,342, filed Aug. 23, 1985, now abandoned.

BACKGROUND OF THE INVENTION

1. Field of the Invention

The invention relates to a method and apparatus for removing unwanted biological tissue. It relates more particularly to surgery using an endoscopic ultrasonic aspirator with an elongated hollow probe and simultaneous irrigation and aspiration, which disintegrates and removes highly compliant tissue from deep within the body through a narrow surgical orifice.

2. Description of Related Art

The endoscopic ultrasonic aspirator (hereinafter "EUA") of the present invention is particularly useful in the field of transurethral resection (TUR) of the prostate gland or other urological surgery, including destruction and removal of bladder stones. More generally, it is useful in any type of surgery in which deep penetration of the body through a narrow orifice is required, for example arthroscopic surgery, diskectomy, or other orthopedic surgery.

In a preferred embodiment of the invention, an ultrasonic probe with a high peak tip velocity is insertable at least about 19 cm into the body for disintegrating compliant tissues, simultaneously irrigating the operating site, and aspirating fluid and tissue, through a surgical orifice no more than about 29 mm in circumference, which is the accepted maximum dimension for an instrument to be inserted into the urethra. The circumference of the instrument may be as great as about 29 mm, but preferably is no more than about 25 mm.

A unit of measurement known as the French is frequently used to denote circumferential size. A sheath size in French is three times the sheath's diameter in millimeters. Thus, a sheath having a circumference of 30 mm has a diameter of $30/\pi = 9.55$ and a French size of $9.55 \times 3 = 28.65$.

Since the 1950's TUR has been the procedure of choice for removal of the diseased prostate gland. In one conventional procedure, the patient is placed in the conventional lithotomy position under spinal anesthesia. An elongated resectoscope with a light source, a telescope, a cutting electrode, and a source of continuous irrigation is inserted into the urethra and advanced to the vicinity of the prostate gland, where access to the prostate is gained through the urethral wall. The cutting electrode is a semicircular wire mounted at the end of a slidable shaft for antegrade and retrograde motion; that is, toward the front and rear of the patient. The electrode is supplied with a pulsed RF current which both cuts and cauterizes tissue. The shaft is spring-biased toward the rear of the patient and is repetitively drawn forward by a trigger-like lever as the electrode slices off small slivers of prostate tissue.

As the tissue is sliced off it is washed into the bladder by the continuous irrigation, which fills the bladder about every 5 minutes. The accumulated water and debris must be removed periodically with a suction device such as the Ellik evacuator, which has a squeeze bulb coupled to a flexible plastic catheter. The resectoscope is removed, the bulb is compressed and the plastic catheter is inserted to the operative site. Then the bulb is expanded to draw out the water and tissue debris.

This traditional procedure has a number of disadvantages that the present invention is intended to avoid. In order for the surgeon to view the operating site, the EUA must be provided with some type of viewing and lighting system. It has been found that, at the present level of optical technology, an adequate endoscopic view of surgical procedures requires an optical relay lens system that uses lenses with a diameter of about 2.5 mm. Since these lenses must be mounted within a rigid tube that also contains illumination fibers, the total diameter of the finished telescope typically measures about 4 mm. Additionally, in order for a hollow ultrasonic tip to remove firm prostatic tissue at an adequate rate (typically from about 5 to about 10 grams per minute), the bore of the tip must also be about 4 mm.

In an endoscopic aspirator, both the telescope and the tip are placed side by side within a sheath. When the endoscopic aspirator is inserted into a patient's body, the sheath protects the surrounding tissue from contacting the ultrasonic tip which vibrates not only at its surgical extremity but also along its entire length.

The use of a loop-shaped electrode for cutting requires antegrade cutting so that removed tissue does not build up in front of the loop and block the viewing lens. However, with antegrade cutting, the loop is always hidden under some thickness of tissue. This leads to the risk that the surgeon's view will be blocked and the urinary sphincter, the bladder wall, or even the intestines may be accidentally damaged. The surgeon can also pierce the prostate capsule, which is the tougher outer skin of the prostate, and injure the blood vessels beyond. Electrical cutting is very fast, so that can occur even with the exercise of due care. Further when the telescope of the EUA is positioned adjacent to the ultrasonic tip, the walls of the ultrasonic tip interfere with the surgeon's view of the operating site.

Also, evacuation must be performed 10 to 20 times, removing the resectoscope each time, and this may take up as much as 20 to 50 percent of the one-hour operating time.

Another disadvantage of the prior procedure is that the continuous irrigation flow described above causes filling and distention of the bladder and absorption of the fluid into the blood, leading to the danger of hypervolemia or hyponatremia. Also, electrical cutting requires the use of a relatively expensive non-conducting fluid medium such as isotonic glycine. If a conducting fluid such as saline is used, the cutting current can be short-circuited away from the work. The fluid must be isotonic to avoid intravascular hemolysis.

Further, the prior procedure is incapable of removing bladder stones, which may necessitate two operations where a single operation would have been preferable.

Since the EUA is frequently used in the field of transurethral resection, the EUA must frequently be inserted into the urethra. Therefore, the circumferential size of the sheath of the EUA is limited by the elastic extension of the urethra which is typically about 30 mm (or about 28 French). Surgeons, however, prefer to use sheaths of smaller size, such as 24 or 25 French, to avoid the occurrence of strictures or contractions of the urethra following excessive endoscopic dilation.

Endoscopic ultrasonic tissue removal and aspiration avoids these disadvantages. Ultrasonic tissue removal has been employed in the past for dissection and removal of biological tissue. However, no ultrasonic instrument has been available to remove highly compliant tissues through a narrow orifice, for example in transurethral prostate resection. The prior art has two principal failings. First, there was no long, slender probe capable of sustaining ultrasonic vibrations at the high tip velocities that are necessary for removal of such tissues. Second, the art has not realized that the most efficient tissue removal is by ultrasonic vibrations causing cavitation of the fluid within the cells. Such vibrations should preferably be in the 10-20 kHz range, although other frequencies may be used. The term "ultrasonic" will be employed herein to refer to all the frequencies of interest, including some frequencies in the audible range.

In one early development, Von Ardenne and Grossman reported in 1960 on the use of ultrasonic vibration to assist in inserting small-gauge wire probes and hollow needles into the skin. They mention constructing an ultrasonically vibrating needle connected to a syringe which is adapted to inject or withdraw fluid or other material from adjacent the tip of the needle. They employ a velocity transformer of the exponential type and operate at a frequency of about 25 kHz with a tip excursion of about 10-100 microns.

Also in 1960, Watkins et al. reported the use of an ultrasonic chisel to fracture and remove calcium deposits from cardiac valves. The authors state that their technique is unusable on soft, flexible tissues since the belief at the time was that such tissues are relatively undisturbed by ultrasonic vibration. Their apparatus operates at about 26.5 kHz with a tip excursion of about 38 microns.

Ultrasonic energy has also been employed to cavitate a liquid medium to burst and destroy suspended microorganisms for either sterilization or extraction of the protoplasm. This technique typically employs a solid round metal horn immersed in the liquid medium and vibrating at perhaps 20 kHz with a stroke of about 20-40 microns. It operates by cavitating the water around the cells, rather than the intracellular water.

Prior patents have disclosed surgical instruments in which ultrasonically vibrating tools remove unwanted biological material while providing irrigation of the work area and aspiration of fluids and removed material. See, for example, U.S. Pat. No. 2,874,470 to Richards, U.S. Pat. No. 3,526,219 to Balamuth, U.S. Pat. No. 3,589,363 to Banko and Kelman, and U.S. Pat. No. 4,063,557 to Wuchinich et al. The Richards device is a dental instrument which operates above the audible range, preferably at about 25 kHz, with an amplitude of about 10 microns. In the Balamuth '219 device, a sharp-edged tool vibrating at about 25 kHz directly contacts tissue to "chop" it. In the Banko and Kelman '363 device, a thin-walled tubular tip which vibrates with an amplitude of about 50-70 microns breaks apart and removes relatively hard biological material such as cataract material in the lens of the human eye. The Wuchinich et al. '557 patent discloses a device for removing compliant tissues such as neurological neoplasms, employing a magnetostrictive transducer which vibrates at about 25 kHz with a stroke of about 25 microns. A stepped and tapered mechanical transformer increases the stroke to about 125-400 microns.

None of these devices has been capable of providing sufficient tip velocity and a long and narrow enough probe to perform endoscopic surgery. The greatest insertable distance available with prior ultrasonic surgical instruments has been about 7-8 cm. More particularly, prior devices have been unable to exert sufficient sound pressure on compliant cells in a biological tissue structure such as a glandular tumor to produce cavitation in the intracellular fluids of the cells, or to disintegrate them in any fashion.

SUMMARY OF THE INVENTION

The prior art devices being ineffective, it was desired to improve the speed and efficiency of tissue removal, and provide a vibrating probe longer and faster than was previously available for endoscopic surgery.

Experiments by the inventors have shown that the effectiveness of ultrasonic vibration on biological tissues is related to the water content of the tissue. Tissues that have been allowed to dehydrate are much less amenable to attack and removal by vibration than those that are fresh or have been kept moist. It has also been seen that the walls of blood vessels or the connective tissue overlying muscles and brain tumors are not affected by an ultrasonically vibrating tool nearly as much as soft, fleshy specimens such as neoplasms, or muscle tissue. Since the intracellular water content of the unaffected tissues is much lower than that of the tissues that are affected to a greater extent, this "tissue-differential" or "tissue-selective" effect seems to be related to the water content of tissue.

The present inventors conceived that the tissue-differential effect could give ultrasonic aspiration a unique advantage in endoscopic surgery, since the undesired tissue could be removed without risking injury to other structures under difficult conditions of visibility and access to the operating site.

Because of the relationship between tissue removal and water content, the inventors hypothesized that the physical mechanism causing the parting of tissue was the destructive effect of intracellular cavitation, i.e., the formation, due to rapidly varying pressure, of microscopic vapor bubbles in the intracellular fluids. For a given level of pressure in a fluid, the degree of cavitation is determined by a number of the fluid's physical properties, for example temperature, surface tension, viscosity, vapor pressure and density. Very important is the dependence of cavitation upon (1) the applied pressure, and (2) the frequency at which the applied pressure oscillates. Studies have suggested that the intensity of cavitation in water increases as the frequency of vibration is lowered. This hypothesis was tested by setting up two transducer tips having exactly the same size but providing different frequencies of pressure oscillation. Since the pressure produced by oscillating motion is proportional to the velocity of this motion, both tips were operated with the same velocity at the point of tissue contact. One tip vibrated at 40 kHz, while the other vibrated at 20 kHz. On the same specimen, the use of 20 kHz vibration approximately doubled the rate of tissue removal—confirming a relation to cavitation, and disproving any suggestion that tissue fragmentation could be enhanced only by increasing vibrational amplitude or acceleration. Similarly, it was found that the cavitation rate again doubles when the frequency is further lowered to 10 kHz. Below a threshold of 10 kHz, the rate remains constant.

There is also a pressure threshold, below which it is not possible to cavitate a given fluid. This threshold also decreases with frequency down to about 10 kHz, below which the pressure threshold does not decrease further.

For these reasons, the frequency regime preferably embraced by this invention extends from 10 kHz to 20 kHz, and thus encompasses part of the aural spectrum, although of course lower or higher frequencies could be used. It was previously assumed that the use of audible frequencies would be irritating and dangerous to the surgeon and that the frequency should be restricted to the inaudible range above 18 kHz. Longer wavelengths were also discouraged because a half-wavelength transducer at 20 kHz would be about 5 inches long, approximately the maximum length for convenient hand-held use.

However, the present inventors have found that in an endoscopic device different considerations apply than those previously known to the art. In endoscopic surgery most of the vibrating components are placed within a natural body orifice, such as the urethra, so that the radiation of aural sound is greatly damped by the intervening body tissues. In some percutaneous applications, such as arthroscopic surgery, while only part of the instrument may be placed within tissue, the sound radiated from the exposed parts is minimal and can be effectively limited if desired by the use of absorbing sheaths and enclosures over the transducer and a portion of the tip.

Even with the use of the most advantageous frequencies, the maximum possible tip velocity should also be employed to further enhance pressure and hence cavitation. Since pressure is related to the velocity of the transducer by the conventional formula P=ZV, where Z is the acoustic impedance of the fluid, the relationship between cavitation and pressure translates into a direct dependence of cavitation upon velocity. Cavitation is believed to be relatively independent of both the acceleration and the amplitude of vibration.

Velocity cannot be increased without limit, however, since there is a definite physical limit to the velocity at which robes or tips made out of known materials can be safely vibrated. The mechanical stress at a given point within a vibrating tip is directly related to the tip velocity at that point. Increasing the tip velocity correspondingly increases the stress within the tip until it exceeds the strength of the crystalline bonds within the tip material and the tip fractures. Special designs can be developed to permit great tip velocities for a given maximum stress, but prior art designs have invariably increased the cross-sectional size of the tip and have been difficult to fabricate. Therefore, in addition to lowering the frequency of vibration, an important object of the invention is also to increase the cavitation rate by providing improved apparatus to enhance the available tip velocity without exceeding the maximum permissible stress on the tip material.

For a regular structure, such as a tube with constant cross-section, the tip velocity at a given point is related to stress according to the equation s=pcv, where v is the velocity (distance per unit time), p is the density of the material of which the tip is made (mass per unit volume), c is the velocity with which extensional sound waves travel in the tip (distance per unit time) and s is the stress is the tip (force per unit area). For titanium, which is capable of bearing the greatest stress of any commonly available material, the above relation means that maximum permissible velocity is approximately 1270 centimeters per second. However, it is known that effective removal of living tissue preferably employs velocities of at least about 2540 centimeters per second.

To improve tissue removal, greater tip velocity may be obtained by use of a velocity transformer having non-uniform cross-section. The equation above applies only to uniform structures, such as tubes having a constant cross-sectional area. If the tube is made non-uniform, the equation is modified by a shape factor M, sometimes called a figure of merit:

$$s = \frac{pcv}{M}$$

Depending upon how the alteration is made, the shape factor either increases or decreases the available tip velocity for a given maximum stress. Of interest here is finding a tip design whose shape factor is greater than one.

It is clear from the modified equation that for a given maximum allowable stress, the tip velocity may be increased over that obtainable in a uniform tube by a factor of M.

There are a variety of tip designs in which the tip's cross-sectional area varies with respect to its length to provide a value of M that is substantially greater than one. For example, exponential tips whose cross-sectional area varies along its length as $$\text{Area} = A_o e^{-aL}$$

where e is the natural base, Ao and a are constants and L is the distance from the point in question to the end of the tip, can theoretically provide a shape factor equal to e or 2.7. However, to obtain this value of M requires that the tip begin and end with drastically different diameters. A tissue removal device employing an exponential design with a shape factor of 2, which could safely produce a tip velocity of 25.4 m/sec, would begin with a diameter roughly five times that of the surgical end. In an endoscopic device that must extend several inches into a narrow body orifice, an exponential design is impractical. If built to accommodate the limitations of human anatomy, its tip would be too small to remove tissue at a practical rate.

It has been found that the most space-efficient design for increasing the value of M from 1 to approximately 2 employs the use of a constant-stress velocity transformer coupled to a constant-diameter velocity transformer. In a uniform tube executing extensional vibration, the stress obeys the relation $$s = \sin \pi x/L$$

where x is the distance to the point in question from one end of the tube, and L is the total length of the tube. It can be seen from this relation that the stress is maximum when x=L/2. Thus it would be desirable to provide at the working end of a surgical probe having length L/2 a further section with varying cross-sectional area, so that for values of x greater than L/2 the stress will remain constant at the maximum permissible value.

Also, such a design would produce the greatest possible extension for a given maximum stress. Since Hooke's law dictates that the extension of each portion of the transformer is proportional to stress, and since the stress is constant, the extension linearly increases along the tip length beyond its midpoint.

It will be shown below that such a tip, in the region designed for constant stress, has a cross-sectional area obeying the relation Area=$Be^{-by^2}$ where B and b are constants and y is the distance from a given point to the end of the tip. This mathematical function is known as the Gaussian function, after the mathematician Gauss who studied its properties. Consequently, the constant-stress tip will be referred to as a Gaussian resonator. Gaussian resonators provide a significant improvement over any alternative design since they can be made with diameters that can be accommodated by the human anatomy with a sufficiently large tissue contact area and aspiration port to permit efficacious tissue removal, and can exhibit a shape factor of 2, making it possible to practically attain a velocity of 25.4 meters per second in an endoscopic or percutaneous device. Further, the Gaussian design does not require a wide disparity between the two end diameters.

The cross-sectional area progressively decreases along the length of the resonator so as to keep the stress constant, but it need not do so very close to the tissue-containing end of the tip. Since there is no load on this point, the stress is zero, so the very end of the tip need not be designed to sustain the same stress but rather may be contoured and rounded to gradually lower the stress to a value of zero.

The mathematical basis for providing a Gaussian resonator in the EUA is as follows: well-established acoustical principles establish the parameters that affect the maximum velocity available from slender bars undergoing simple extensional vibration. For a uniform bar, with both ends free, the maximum obtainable velocity is directly related to the maximum stress that the material of which the bar is made can safely withstand:

$$V_{max} = \frac{S_{max}}{pc} \quad (1)$$

where $V_{max}$ is the velocity (distance per unit time), $S_{max}$ is the safe stress limit (force per unit area), p is the material density (mass per unit volume), and c is the velocity with which extensional waves travel in the material (distance per unit time). Since metals are the only practical materials capable of sustaining the high-level acoustic vibration of interest, and since c is approximately the same for all these metals, to obtain the largest possible value of $V_{max}$, a material should be selected that has the highest possible strength-to-weight ratio ($S_{max}/P$). This material has been well established to be aircraft titanium. The safe value of vibrational stress has been determined by experimentation to be one-third the value of the yield stress (the stress at which the metal begins to irreversibly deform). When $V_{max}$ is computed using the appropriate values of $S_{max}$, p and c, it is found that $$V_{max} = 1219 \text{ cm/sec.} \quad (2)$$

for a uniform bar of aircraft titanium.

However, this velocity provides only a small degree of soft tissue dissection, even when the frequency of vibration is lowered to enhance cavitation of intracellular water. A value approximately twice that given by Eq. 2 is desirable to effectively disintegrate such tissue. Consequently a velocity transformer is desirable that approximately doubles the value of $V_{max}$ without increasing the maximum stress above $S_{max}$. It is also desirable, in an endoscopic device, for this velocity transformation to be accomplished within a narrow circular channel preferably about 8 millimeters in diameter, of which about 4 millimeters constitutes a circular aspiration bore. It is therefore important that the velocity be increased with a minimum change in cross-sectional area so that the entire resonator can be placed within the endoscope over a length of at least about 17-19 centimeters.

FIG. 1 shows a hypothetical velocity transformer consisting of a uniform section one-quarter wavelength long, followed by an integral second section of length L. FIG. 2 illustrates various possible stress distributions in this bar for different hypothetical cross-sectional variations of the second section. The velocity at any point to the right of the uniform section can be written as $$v(x) = [-2\pi f/E] \int_o^x s(x)dx. \quad (3)$$

where $s(x=o)=S_{max}$, $S(x=L)=0$, f is the frequency of vibration (cycles per unit of time), and E is the elastic constant or Young's Modulus (force per unit area). Thus, the velocity distribution along the section can be computed directly from these stress distributions. The velocity at any point is proportional to the area under the stress curves to that point. FIG. 3 illustrates these corresponding velocity distributions. Curve 1, although it produces the largest end velocity, exceeds $S_{max}$ and therefore is not a practical choice. Curves 2 and 3 produce safe stress distributions, but do not result in the maximum attainable end velocity. The areas under these curves in FIG. 2 are less than the areas under curves 1 and 4.

Curve 4 alone increases the velocity most rapidly while maintaining a safe operating stress. Curve 4 represents a constant stress level in the section, except at the terminus, which is free and therefore is not subject to any force.

It remains to be determined how to contour the second section so as to produce this optimum stress distribution. The velocity distribution in an extensionally vibrating slender bar is related to the stress and cross-sectional area as $$[2\pi f]p \cdot A(x)v(x) = A(x) \cdot \frac{\partial - s(x)}{\partial x} + s(x) \cdot \frac{\partial A(x)}{\partial x} \quad (4)$$

Since $s(x) = S_{max}$, for $0 \leq x \leq L$, $\quad (5)$ and since $\frac{\partial s(x)}{\partial x} = 0$ $\quad (6)$ then v(x) and s(x) are related by Eq. 3 with $s(x)=S_{max}$, which results in $$v(x) = \frac{-2\pi f}{E} \cdot S_{max}x \quad (7)$$

Substituting Eqs. 5, 6 and 7 in Eq. 4, there results the condition:

$$\frac{1}{A(x)} \frac{\partial A(x)}{\partial x} = -[2\pi f/c]^2 \cdot x \qquad (8)$$

which, when integrated between $A(x=0)=A_o$ and $A(x)$, and between $x=0$ and $x=x$, yields $$A(x) = A_o e^{(-k^2 x^2/2)}, 0 \leq x \leq L, \text{ where } k^2 = [2\pi f/c]^2. \qquad (9)$$

Thus, to obtain the optimal velocity transformation, the cross-sectional area of the resonator must progressively decrease from its value at $x=0$ as dictated by Eq. 9, which is the Gaussian function.

There is no theoretical limit to the amount the velocity may increase so long as $A(x)$ satisfies Eq. 9. As a practical matter, the resonator is hollow, and ultimately the wall thickness required for ever-diminishing values of A would produce a structure insufficiently strong for the rigors of medical use. However, the Gaussian resonator does exhibit a velocity transformation factor of at least 2 with an acceptable starting cross-sectional area $A_o$, making practical the attainment of tissue dissection with an endoscopic device.

Constant-stress amplification can also be achieved in a uniform structure such as a cylindrical tube by varying the elastic constant E, or both the elastic constant E and the density p, over the length of the structure, without varying the cross-sectional area.

An example is a system is which density is proportional to the elastic constant, that is, p=nE where n is a constant. It is found that constant stress can be obtained in such a system if E is varied according to the Gaussian function:

$$E + E_o e^{-n(2\pi fx)2/2}, \qquad (10)$$

where $E(x=0)=Eo$. Thus, the elastic constant E decreases from the vibration input to the free end of the resonator. Under these conditions, $$v(x) = -2\pi f S_{max} \int_0^x [s(x)/E(x)] \, dx. \qquad (11)$$

Since $S(x) = S_{max}$ in a constant-stress system, $$v(x) = -2\pi f S_{max} \int_0^x 1/E(x) \, dx. \qquad (12)$$

Since $E(x)$ is a decreasing function, the integral in Equation (12) increases at a faster rate than it would if $E(x)$ were a constant function as in Equation (3) above, so greater velocity amplification can be expected under these conditions than in a system in which cross-sectional area is varied to achieve constant-stress conditions.

According to one aspect of the invention, high-frequency vibration apparatus comprises a vibration source, for vibrating with a first amplitude, a first transformer for amplifying the vibrations, and a second transformer for amplifying the vibrations of the first transformer, the second transformer being elongated and when vibrating having a substantially constant mechanical stress level in substantially all of its length. The second transformer may have a cross-sectional area that varies from its input end to its output end so as to provide such substantially constant mechanical stress level. The cross-sectional area of the second transformer may vary according to the Gaussian function. Alternatively, the substantially constant stress level may be provided without varying the cross-sectional area by varying the elastic constant of the material of the transformer, or both the elastic constant and density of the material.

A further form of the invention includes a handpiece, a vibration source for vibrating with a selected wavelength and with a first amplitude, a first transformer for amplifying vibrations from the vibration source, and a second transformer for amplifying vibrations from the first transformer, the first transformer having an input section relatively large in cross-sectional area and coupled to the vibration source, and also having an output section, and the second transformer having an input end coupled to the output section of the first transformer, and having an output end vibrating in response to such received vibrations.

According to a further form of the invention, an endoscopic ultrasonic aspirator comprises a hollow handpiece, an elongated sheath having a hollow bore running from the interior of the handpiece to a working end away from the handpiece, a vibration source powered by alternating current, an elongated tool coupled to the vibration source and passing through the hollow bore of the sheath to a work site for transmitting such vibrations, viewing means extending from the handpiece to the work site, means for supplying fluid to a fluid space between the tool means and the hollow bore of the sheath, and fluid detection means for detecting the presence of fluid in the fluid space and terminating the supply of alternating current to stop the vibrations when such fluid is not present.

In another form of the invention, an apparatus for removal of unwanted biological material comprises a handpiece; an elongated sheath extending from the handpiece and having a hollow bore; a vibration source in the handpiece; first and second transformers in the hollow bore for amplifying vibrations from the source to a sufficient velocity to disintegrate unwanted tissue, the vibration means and the two transformers being elongated and having a continuous hollow bore extending along a common longitudinal axis to form (1) a first fluid passage in a space defined between the transformers and the sheath, and (2) a second fluid passage along the common longitudinal axis; means for introducing fluid into one of the fluid passages to irrigate an operating site adjacent a working tip of the second transformer; and means for applying suction to the other of the fluid passages to remove such fluid and such disintegrated unwanted tissue from the operating site. According to a further aspect, the means for applying suction includes a biopsy valve coupled to the fluid passage to which suction is applied for selectively diverting fluid and tissue therefrom, and trap means for receiving and filtering the desired fluid and tissue that has been selectively diverted.

A further aspect of the invention is a method for removing cellular material from a compliant tissue relatively deep within a biological body through a narrow orifice, comprising inserting an elongated surgical instrument into the orifice, with a working tip located close to the material to be removed, and vibrating the working tip so as to disintegrate such material. A further method provides removal of cellular material from a compliant issue at an operating site at least about 8 cm deep within a biological body through a narrow orifice, preferably no more than about 29 mm in circumference.

comprising inserting a narrow elongated surgical instrument at least about 8 cm deep into the body through the orifice with a working tip of the instrument being located close to the material to be removed, and vibrating the working tip longitudinally so as to produce pressure waves to disintegrate the material. The vibration of the working tip advantageously cavitates the intracellular fluids in such material to destroy its cells. Vibration is preferably at about 10 to 20 kHz, with a longitudinal stroke of at least about 350 microns, Preferably at least about 700 microns; and with a maximum velocity of at least about 1,000 cm per second, preferably at least about 2,000 cm per second.

A further form of the invention is a method of removing cellular material from a compliant tissue at an operating site deep within a biological body through a narrow orifice, including providing a surgical instrument having an elongated sheath at least about 8 cm in length and no more than about 29 mm in circumference, the sheath having a hollow bore; locating an elongated probe within the hollow bore, the probe having a working end projecting beyond the end of the sheath and a hollow bore therethrough, thereby forming a first fluid passage in the space between the probe and the sheath, and a second fluid passage within the probe; inserting the sheath into the body orifice with the working end of the probe close to the material to be removed; introducing a fluid into one of the fluid passages to irrigate the operating site; vibrating the probe longitudinally so as to produce pressure waves sufficient to disintegrate the cells of the material to be removed; and applying suction to the other of the fluid passages to withdraw the fluid and the matter to be removed from the operating site.

Employing the invention in transurethral resection of the prostate achieves many benefits such as (1) the tissue-differential effect, (2) a thermal cauterization and an absence of necrosis, which should greatly accelerate healing, (3) retrograde motion of the instrument permitting direct visualization of the procedure, (4) capability of removing bladder stones or the like, and (5) reducing the duration (and hence increasing the safety) of the procedure by increasing the tissue removal rate and permitting continuous operation.

The tissue selectivity of the endoscopic ultrasonic procedure reduces the risk of piercing the prostate capsule or bladder unless the instrument is forced by the operator. Any obstructions such as blood vessels are easily felt by the operator in that the handpiece is directly mechanically connected with the working tip, leading to an inherently safer procedure that can be used with less training than the prior procedure.

The ultrasonic procedure also causes minimal microscopic tissue distortion, allowing more precise histological diagnosis. The aspirated tissue can be diverted quickly to a biopsy trap of the system and removed for analysis. A further advantage is the elimination of electrical currents passing through the patient's body, avoiding the risk of shock effects, burns, or the obturator nerve reflex.

Employing continuous aspiration of the debris and water shortens the operative time to as little as one-half hour. This results in diminished operative bleeding, as well as generally decreasing operative risk to the patient. Further reduction of bleeding results from the cauterization effect of the friction of the moving tip on adjacent tissue.

Also, using ultrasonic tissue removal combined with continuous irrigation and aspiration permits retrograde cutting, giving the surgeon better visibility of what lies in the path of the cutting edge. Since the pieces of removed tissue are small they are easily aspirated, permitting the surgeon to take one continuous cut with good visibility for any length of prostate tissue to be removed.

The present invention also relates to an endoscopic ultrasonic aspirator with a tip having a reduced circumference which also provides the surgeon using the aspirator with an increased view of the operating site.

The invention further relates to an improvement of an endoscopic ultrasonic aspirator of the type which includes a resonator having a vibrating tip for removal of biological material, means for delivering fluid to the tip, means for removing the fluid and removed biological material, and means for viewing the operation of the vibrating tip. This improvement comprises open channel means connected to the resonator tip to facilitate viewing of the tip during use and means for supporting the open channel means and forming a passage to assist in the proper operation of the aspirator as to the removal of the fluid and removed biological material. If desired, the entire length of the resonator can be configured and dimensioned in the form of open channel means so that the viewing means can be partially received, held and supported by the open channel means, thus minimizing the size of the aspirator. Preferably, the open channel support means is a resilient plug and the channel means has a U or V shaped cross section.

According to a preferred embodiment of the present invention, the tubular ultrasonic tip of the aspirator is cut open along its length. The telescope is then suspended within the cut-out portion of the tip. The end of the ultrasonic tip thus has a U shape in cross-section with the telescope being suspended within the U. As a result, the under-surface of the telescope partially closes off the opening of the U shaped tip so that a cross-section of the opening at the tip near its operational end has a crescent shape.

Because the telescope is partially inserted into the end of the ultrasonic tip, the overall circumference of the end of the aspirator of the present invention is less than that of the end of an aspirator in which the ultrasonic tip is circular in cross-section where the telescope is placed adjacent to the ultrasonic tip. Additionally, since the upper portion of the ultrasonic tip adjacent to the telescope has been removed, the surgeon's view of the operating site is not obstructed by the ultrasonic tip. To ensure that the relative positions of the telescope and the ultrasonic tip do not change, a plug may be inserted between the telescope and the U shaped tip. The ultrasonic tip and plug are then mounted within a sheath or lower lumen which is attached to the upper lumen in which the telescope is mounted.

Other objects, features, and advantages of the invention will be seen in the following detailed description of preferred embodiments, with reference to the accompanying drawings.

BRIEF DESCRIPTION OF THE DRAWINGS

FIG. 5A is an elevational view of a resonator assembly including a transducer and first and second velocity transformers for use in the EUA of FIGS. 4A and 4B;

FIG. 5B is a graph showing extension and stress distributions in the components of FIG. 5A;

FIG. 5C shows an alternate resonator assembly;

FIG. 5D shows another alternate resonator assembly;

FIGS. 10A and 10B together form a block diagram of an ultrasonic power supply for use with the EUA;

FIG. 11 is a cross-sectional view of the EUA taken along line 11—11 of FIG. 4A;

FIG. 12A shows schematically an irrigation system for use with the EUA;

FIG. 14 is perspective drawing of an embodiment of the open channel endoscopic ultrasonic aspirator of the present invention;

FIG. 15 is a cross-sectional view of the embodiment of FIG. 14 taken along the line 15—15;

FIG. 16 is a cross-sectional view of the embodiment of FIG. 15 taken along the line 16—16;

FIG. 17 is a cross-sectional view of the embodiment of FIG. 15 taken along the line 17—17; and FIG. 18 is a cross-sectional view of the embodiment of FIG. 15 taken along the line 18—18.

DETAILED DESCRIPTION OF PREFERRED EMBODIMENTS

Figure 1:
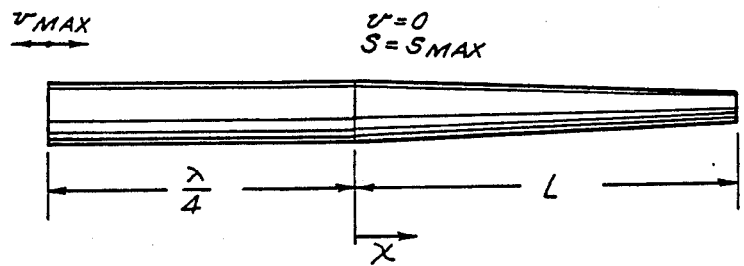
FIG. 1 shows a hypothetical extensional resonator for use in illustrating the background of the invention.
Figure 2:
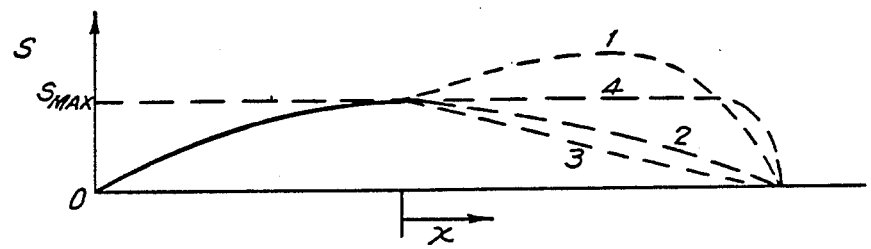
FIG. 2 shows a family of curves illustrating possible stress distributions in the resonator of FIG. 1.
Figure 3:
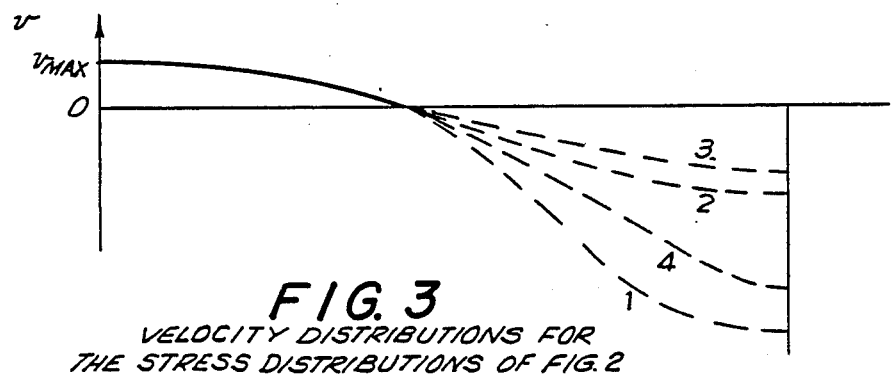
FIG. 3 shows a family of curves illustrating velocity distributions corresponding to the stress distribution curves of FIG. 2.
Figures 4A, 4B:
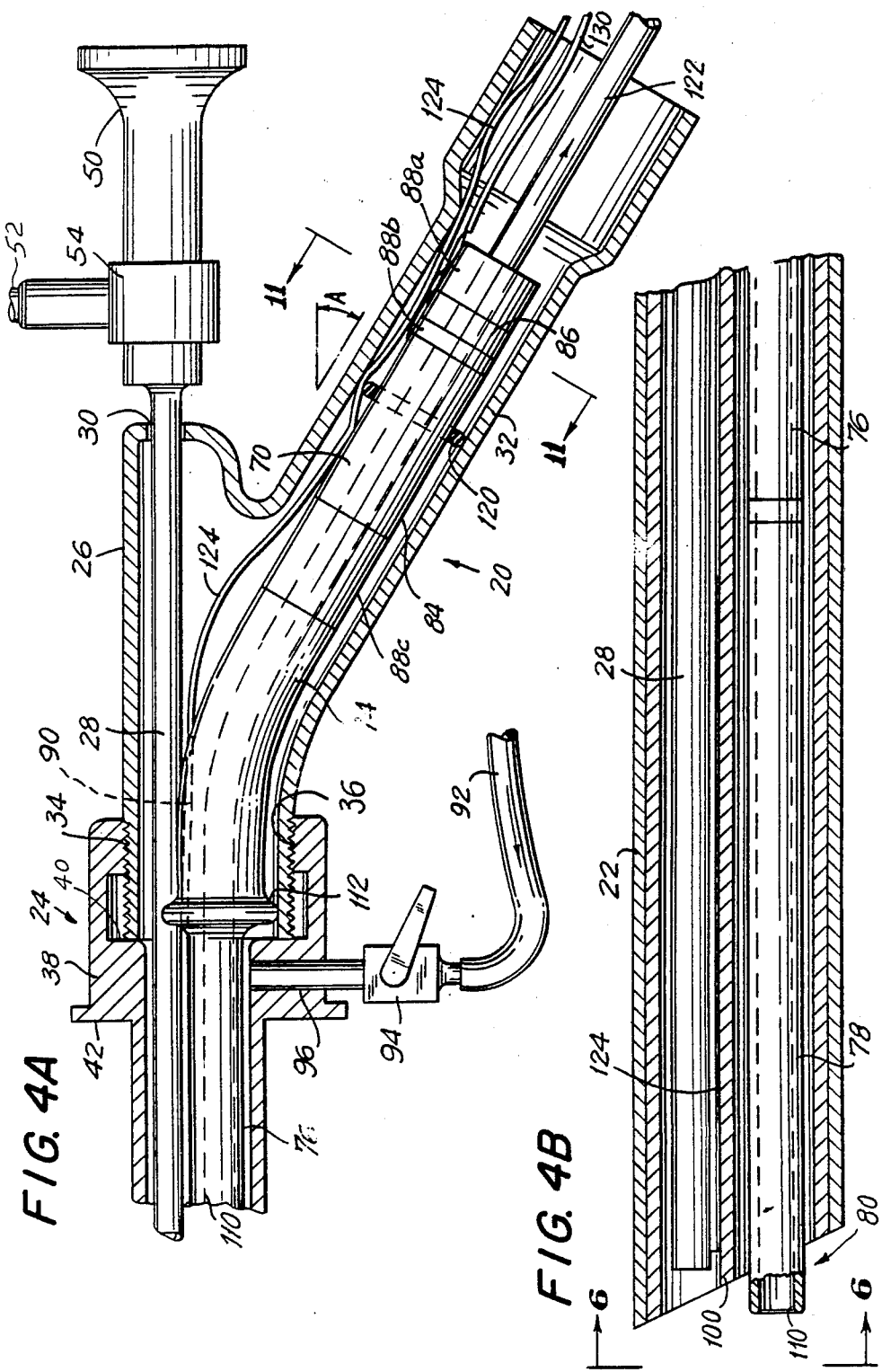
FIGS. 4A and 4B together form a view, partly broken away, of an endoscopic ultrasonic aspirator (EUA) according to an embodiment of the invention.

FIGS. 4A and 4B show an endoscopic ultrasonic aspirator according to a preferred embodiment of the invention. A handpiece 20 is located at what will be referred to as the rear end of the device. A sheath 22 extends from the handpiece 20 toward what will be referred to as the working end of the device. A stop assembly 24, integral with the sheath 22, couples the handpiece to the sheath. The handpiece is preferably plastic and the stop assembly and sheath are preferably metal. The EUA also includes a straight telescope 28 which runs horizontally from the rear end to the working end of the EUA. A horizontal upper lobe 26 of the handpiece 20 contains an aperture 30 through which the telescope passes to the exterior of the handpiece. The handpiece also has a lower lobe 32 which forms an angle A with the upper lobe 26. Angle A may advantageously be about 20 to 45 degrees, its purpose being to allow various components to be located within the handpiece without interfering with the straight horizontal line of sight occupied by the telescope.

The sheath 22 is assembled to the handpiece 20 by means of a stop assembly 24, which is integral with the sheath 22 at its rear end. The stop assembly 24 is generally cylindrical and has a circular aperture in its rear side with inward-facing threads 34. The handpiece is circular at its forward end and has outward-facing threads 36 which are adapted for screw-mounting in the threads 34 in stop 24. The stop 24 has a forward portion 38 with annular faces 40 and 42 which face rearward and forward, respectively. The handpiece is screwed into the rear aperture 30 of the stop assembly until it comes into contact with the rear face 40. The front face 42 of stop 24 limits the distance to which the working end of the sheath 22 of the EUA can be inserted into a surgical orifice.

Figure 7:
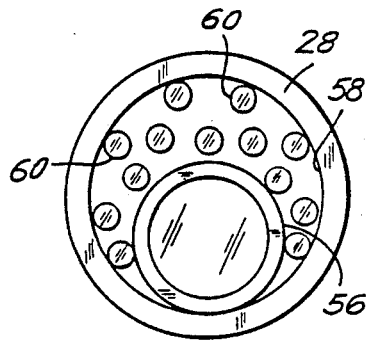
FIG. 7 is a detail of FIG. 6 showing an end view of telescope 28 of the EUA.

The telescope 28 has at its rear end an eyepiece 50 and a cable 52 for supplying electrical energy to an electro-optical light source 54. From the eyepiece the telescope extends forward in a straight line of sight to the working end of the EUA. The design of the telescope is shown in more detail in FIG. 7. The telescope includes a cylindrical lens system 56 which is located adjacent the lower portion of the cylindrical inner surface 58 of the cylindrical telescope 28. In the crescent-shaped space between the inner surface 58 and the lens system are disposed optical fibers 60 which carry light from the light source 54 to the working end of the telescope. Other illumination sources may be provided. In this embodiment, the outside diameter of the telescope 28 is approximately 3-4 mm, and the outside diameter of the lens system 56 is perhaps 1.7-2.7 mm, depending on the size of the overall telescope 28.

Disposed within the handpiece and sheath is a resonator assembly generally designated 68. The resonator assembly 68, which is seen more clearly in FIG. 5, includes a piezoelectric transducer 70; a first velocity transformer 72 having a relatively thick curved input section 74 coupled to the transducer for receiving vibrational energy therefrom, and an integral narrower output section 76 extending forwardly of the input section 74; and, integrally connected to the forward end of the output section 76, a second velocity transformer 78, which extends from the output section 76 to the working end of the EUA and protrudes slightly beyond the sheath 22. The transducer's length is substantially one-half of the wavelength of the vibrations employed in the device. Thus, the transducer has vibrational antinodes (loops) at its ends and a vibrational node halfway between its ends. The length of the curved input section 74 of the first transformer 72 is one-quarter wavelength; thus, its point of connection with the transducer 70 is an antinode, and the point of connection to the output section 76 is a vibrational node. The length of the output section 76 is one-half wavelength. Thus an antinode is at the center of this section, and a node exists where it is connected to the second velocity transformer 78.

The second transformer 78 is of the Gaussian type described above. As seen in the schematic graph in FIG. 5, there is little longitudinal extension and little stress in the input section 74, because it is relatively massive and a substantial amount of its vibration is flexural. Stress is high at both ends of the output section of the first transformer, but is zero at its center point, which is a vibrational antinode or loop with greatest longitudinal extension. The stress in the output section 76 is at the maximum permissible level for the material and design employed, in other words $S_{max}$, as defined above. The Gaussian resonator 78 exhibits constant stress at this same level $S_{max}$ throughout most of its length, almost to the tip 80 at its working end. The stress near the tip 80 is substantially zero, since there is ordinarily little or no load on the tip.

Figure 6:
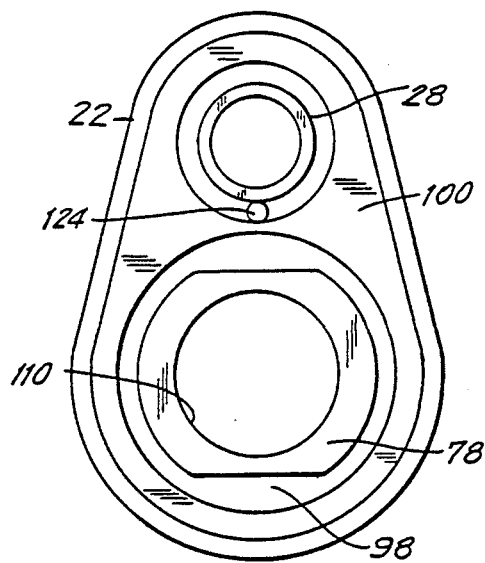
FIG. 6 is an end view of the EUA taken along line 6—6 in FIG. 4B.

As seen in FIG. 6, the second transformer 78 and also the output section 76 are not round. Rather, flats are formed in the top and bottom of these members to provide ample water passages without substantially changing their vibratory characteristics. The central bore 110, however, is substantially circular, with an inside diameter of perhaps 4.33 mm (13 French).

The working end 80 need not lie in a vertical plane as shown, but may be angled or otherwise shaped if desired in a particular application.

The combined length of the output section 76 and the second transformer 78 is advantageously about 19 cm. If desired, it could be lengthened by any integral multiple of one-half wavelength, which at about 20 kHz is about 13 cm.

A piezoelectric transducer such as is used herein typically has a maximum vibration amplitude of about 23 microns. At the frequencies of interest, tip vibration at the necessary velocity entails an amplitude of about 350 microns. The resonator assembly 68 provides this 15-fold increase in vibration amplitude.

A groove 90 is formed in the top of the transformer input section 74 and is sized to accommodate the telescope. The groove 90 permits the telescope to be located closely parallel to the transformer sections 76 and 78 within the forward end of the sheath, without interfering with the input section 74, to achieve a compact and narrow sheath.

The letter R in FIG. 5A refers to the radius of curvature of the curved input section 74. This radius must be small enough so that the handpiece is curved far enough below the line of sight of the telescope, desirably at least about 20 degrees, to achieve a compact and easily handled unit. A radius R of about 5 cm advantageously gives an angle of about 40°. At an operating frequency of 20 kHz, 5 cm is about 0.2 times the wavelength. Preferably, the radius R should be no smaller than about 0.1 times the operating wavelength to avoid excessive energy losses. The radius should also be less than about 0.5 times the wavlength in order to give a usable angle of offset of about 20° over the length of the input section 74, which is about 6 cm. The curvature of the input section is not necessarily circular; thus, the radius R as defined herein is an approximation.

FIGS. 5C and 5D show alternate resonator assemblies 68c and 68d. In FIG. 5C, a first transformer 72 is coupled to a transducer 70. As in the previous embodiment, the first transformer is a half-wave stepped transformer. Coupled to the working end of the first transformer is a second transformer 78c, which has constant cross-sectional area. Velocity amplification is obtained by increasing the elastic constant of the material in the second transformer from its point of connection to the first transformer, to its tip 80c. Optionally, the density of the material of the first transformer may be decreased as a function of distance from the first transformer to the tip.

In the embodiment of FIG. 5D, the same second transformer 78c as just described is employed. However, in this embodiment the first transformer 72d, which is curved as in the previous embodiments, is not a stepped transformer. Rather, velocity amplification in the first transformer is obtained by increasing the elasticity of the material of the first transformer and optionally decreasing the density of the material, as a function of distance from the transducer. As seen in FIG. 5D the transducer 70 and the first transformer are not necessarily required to have the same cross-sectional area at their coupling for sufficient energy transfer to be obtained.

Because of the curvature of the section 74, the transformer sections 74, 76, 78 may undergo a certain small amount of transverse, flexural vibrations. However, any transverse components of vibration in the sections 76 and 78 are damped by the presence of irrigation fluid in the surrounding space 98 within the sheath.

Irrigation fluid is supplied through a hose 92, and is controlled by a valve 94. The irrigation fluid flows through a radical bore 96 in the outer portion of the front section 38 of the stop assembly 24. It then passes into the spaces 98 that surround the resonators 76 and 78 within the sheath. As indicated generally in FIG. 6, the sheath has a generally ovoid cross-section. Its circumference should preferably be approximately 25 mm, about the same as the circumference of a circular instrument 8 mm in diameter, such dimension being known in the field as 24 French. If necessary a circumference of about 29 mm, corresponding to 28 French, may be usable. With 28 French or larger instruments, there is a risk of injury to a narrow orifice such as the urethra. The telescope 28 is disposed in the narrower part of the ovoid sheath 22. It is enclosed by epoxy material or the like running along the inside of the sheath to form a partition 100, which forms a watertight compartment for the telescope.

Figure 8:
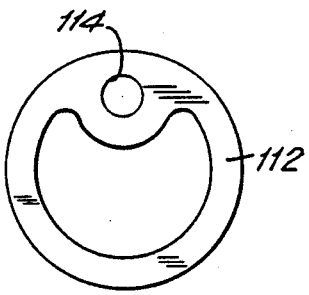
FIG. 8 is a plan view of a sealing ring 112 employed in the EUA.

Irrigation fluid flows toward the working end of the EUA through the space 98 from the vicinity of the stop 24, damping any transverse vibrations of the transformer sections 76 and 78, as well as irrigating an operating site adjacent the tip 80. Auxiliary fluid passages may also be provided. Fluid is prevented from flowing into the handpiece by a sealing ring 112 shown in FIG. 8. The ring is generally O-shaped, but has a smaller aperture formed in its upper portion to accommodate the telescope. The sealing ring 112 seals the annular space surrounding the input transformer section 74 within the handpiece, and provides the hole 114 for water-tight passage of the telescope.

Additional sealing and support is provided by an O-ring 120 disposed about the transducer within the inner wall of the lower handpiece lobe 32. The O-ring 120 is located at the vibrational node at the center of the transducer.

The coupling between the transducer and the input section 74 may advantageously include female threads counterbored into the abutting ends of the aspiration passages 110 of the transducer and the input section, and a hollow threaded stud threaded into both of these. Such a connection allows for a smooth, fine finish of the adjacent faces of these two resonator elements, for good acoustic coupling between the faces.

Referring again to FIGS. 4A and 4B, aspiration is provided through a continuous concentric bore 110 extending from the tip 80 through the second transformer 78, the first transformer 72, and the transducer 70 to a hose 122, which is connected to a source of suction. Other passages may be provided as well. By these means, fluid and removed tissue flow from the operative site and are aspirated through the EUA away from the operating site for either disposal or histological analysis.

The edges of the working end of the second transformer 78 at the tip 80 are rounded, in order to provide tissue removal by cavitation of intracellular water, as discussed previously, without allowing indiscriminate cutting by the tip 80, which could inadvertently injure tissues not intended to be removed.

It is important for any transverse vibration components of the transformer section 76 and 78 to be damped by fluid flowing in the spaces 98, and for vibration to terminate if there is no fluid present. For this purpose, a fluid sensor is provided in the form of an insulated wire 124 running rearward along the telescope, and separated from the fluid space 98 by the partition 100. The wire 124 runs through the hole 114 in the sealing ring 112, and through the groove 90 in the input section 74, to the interior of the handpiece. The wire could also be set into a groove either in the partition 100, in the bore that encloses the telescope, or in the bore that encloses the resonators, if desired. It may also be exposed to fluid if appropriate insulation is provided. The wire is fine enough that it does not interfere with the seal provided by the sealing ring 112. The wire 124 then passes around the O-ring 120 to the exterior of the handpiece. As explained further below, means are provided in the high-frequency power supply circuit to sense the capacitance between this wire 124 and the second transformer 78, which is grounded. If the capacitance increases, which indicates the absence of water, then the vibration of the transducer 70 is inhibited to prevent excessive transverse vibrations and possible damage to the resonator components.

Figure 9:
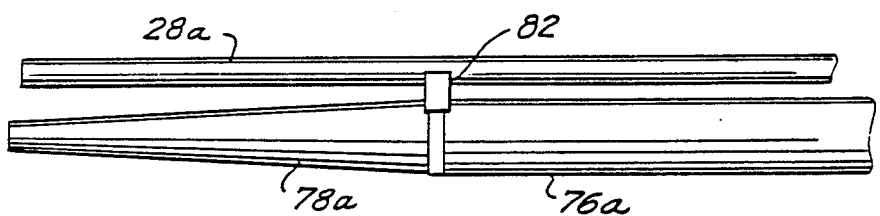
FIG. 9 is an elevational view of part of an alternate embodiment of the invention.

FIG. 9 shows elements of an alternate embodiment of the invention. In this embodiment, there is no partition between the telescope 28a and the irrigation-fluid-containing space that encloses the resonators 76a, 78a. To support the telescope, a quantity 82 of biologically inert silicone rubber adhesive or the like is placed between the telescope and the junction of the resonators 76a and 78a. It is important to employ a flexible adhesive to allow some relative motion, even though this junction is a vibrational node, since each point on each resonator is subject to a small degree of radial vibration, which is inherent in a body undergoing extensional vibration. As each incremental section of a resonator is compressed it instantaneously bulges slightly. Thus, each point on each velocity transformer constantly undergoes a slight radial expansion and contraction. These radial vibrations should be isolated from the telescope. However, there cannot be more than about 250–500 microns of separation between the telescope and the resonators because of the severe size limitation on the sheath. This need for proximity, in view of the further need for vibrational isolation, is resolved by connecting the elements with a flexible adhesive.

Figure 10A:
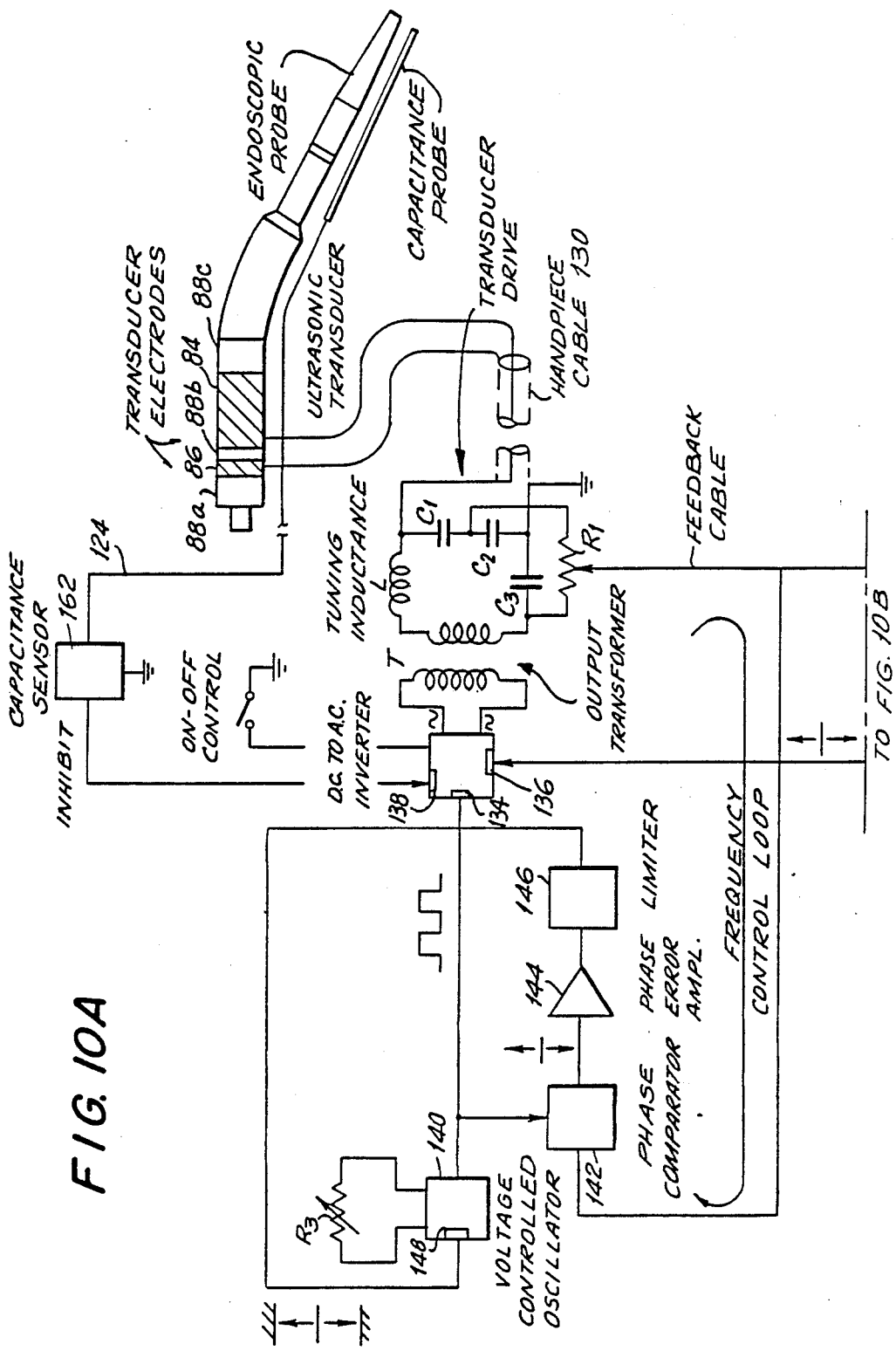

The ultrasonic generator and related circuitry for powering and controlling the ultrasonic transducer 70 are shown in FIGS. 10A and 10B.

The transducer 70 includes an elongated toroidal piezoelectric crystal 71 that is driven by a cylindrical high-voltage electrode 84 and an annular ground electrode 86. (See also FIGS. 4A and 11.) The ground electrode 86 is electrically connected to a conductive lining 116. The lining 116 runs the length of the transducer 70, lining the aspiration passage 110, and is electrically coupled to the velocity transformers. The transducer is insulated by cylindrical insulators 88a, 88b, 88c located at the ends of the transducer and between the electrodes 84 and 86.

The piezoelectric transducer and tip are driven by the generator through a two-conductor coaxial cable 130. It is energized by an AC signal whose magnitude and frequency are controlled by a DC-to-AC inverter 132. This inverter converts an input DC voltage to an alternating current signal having a frequency controlled by an AC signal supplied to its frequency control input 134 and a magnitude controlled by a DC voltage level supplied to the inverter at its magnitude control input 136. The frequency provided at the input 134 is the frequency at which the transducer is caused to vibrate. The DC voltage supplied at the input 136 is that required to maintain a selected amplitude of vibration at the frequency of vibration.

The exciting frequency and voltage are derived from a feedback signal obtained by adding two signals that are proportional to the voltage and current input to the transducer. In FIG. 10, $C_1$ and $C_2$ form a capacitive voltage divider which produces a voltage across $C_2$ that is directly proportional to and in phase with the transducer voltage. The voltage across $C_3$ is proportional to the transducer current, but shifted in phase by 90 degrees. The voltage between the wiper of potentiometer $R_1$ and ground, which constitutes the sum of these two potentials, is the feedback signal. When $R_1$ is properly set, the feedback signal is very low at all excitation frequencies except at the resonant frequency of the transducer, since at resonance the transducer voltage and current are 90 degrees out of phase.

At resonance, when the feedback signal is present, its magnitude is proportional to the amplitude of vibration and its phase exactly equals that of the inverter output signal.

The inductance L reactively cancels the transducer's static capacitance; that is, the capacitance of the cable 130 and the net capacitance of the voltage divider $C_1, C_2$. This capacitance is advantageously neutralized so that the voltage at the wiper of $R_1$ will be proportional to the vibration amplitude and will be very small at frequencies other than resonance.

The feedback signal is fed to two control loops: one for establishing the correct frequency and the other for establishing the desired vibration amplitude. When the aspirator is de-energized there is of course no feedback signal, and some means of starting vibration has to be provided. A predetermined starting frequency is provided by a voltage-controlled oscillator 140. In the absence of any feedback, this oscillator runs at a frequency adjusted by variable resistor $R_3$ in the general range of the expected transducer resonance. Since, in general, this initial exciting frequency is not the resonant frequency, a substantial feedback signal will not be produced. However, acoustic resonators do exhibit some greatly diminished level of vibration at frequencies within about five percent of their actual resonance. Therefore, a small, but detectable, feedback signal is produced.

In the frequency control loop, the feedback signal enters a very sensitive phase comparator 142 which produces a DC voltage proportional to the difference between the phase of the feedback signal and the phase of the output of the voltage-controlled oscillator. The frequency of the feedback signal is the same as that of the oscillator, but the phase is not the same because the frequency is not yet at the resonant frequency of the transducer. The output from the phase comparator is greatly amplified by a phase error amplifier 144 and then passed through a limiter 146 which places upper and lower bounds upon the amplifier's output. This amplified signal, subject to the bounds of the limiter, is then supplied to a steering input 148 of the voltage-controlled oscillator 140, and modifies its output frequency until the phase difference between the feedback signal and the output signal of the VCO is minimized. The VCO frequency that produces this result is the actual resonant frequency of the transducer.

The result of limiting the range of the steering voltage applied to the oscillator at input 148 is to limit the extent to which the frequency can be shifted. In general, a complex acoustic resonator, such as transducer 70, has more than one extensional resonance, at only one of which the desired performance is obtained. Excitation at other resonant frequencies would result in much lower vibration levels and very poor tissue dissection. Because the vibration levels are much lower at these parasitic resonances and constitute a lower overall energy of vibration, if precautions were not taken, the system would naturally tend to operate at frequencies where it did less work. The limiter 146 prevents the oscillator from being driven to frequencies that lie outside a predetermined band which brackets the intended resonance.

In the amplitude control loop, the feedback signal is fed to a rectifier 150 which produces a DC voltage proportional to the magnitude of the feedback signal. A low-pass filter 152 is provided to eliminate any AC components and extract only the direct current component. This signal is then subtracted by a summer 154 from a preselected DC voltage. The difference between these two voltages is greatly amplified by an amplitude error amplifier 156 and is input to the main power supply 160 to control its DC output voltage. This DC output voltage is the source of power to the inverter 132. It is proportional to the magnitude of the inverter's AC output signal, which, in turn, is proportional to the amplitude of vibration of the transducer 70. This amplitude control loop maintains the amplitude of vibration desired by the operator regardless of the power drawn from the inverter 132 by the transducer 70, thereby providing uniform performance in the presence of compliant as well as resistant tissue. Since the power available from the inverter is not limitless, internal circuitry is provided in this component to safely limit the maximum power consumption by the transducer, and thus preclude unsafe power demands through intentional or unintentional abuse. If the power limit of the inverter is reached, the output vibration amplitude is automatically reduced. The amplitude is reestablished at the control setting once the excessive power requirement has been removed.

Also seen in FIG. 10A is a capacitance sensor 162 which measures the capacitance between the capacitance probe 124 and ground. When this capacitance increases substantially, indicating the absence of water surrounding the velocity transformers 72 and 78, the capacitance sensor 162 sets the input level at an input 138 of the inverter 132 to a level that inhibits the inverter and terminates the AC output to the transducer.

Figure 12B:
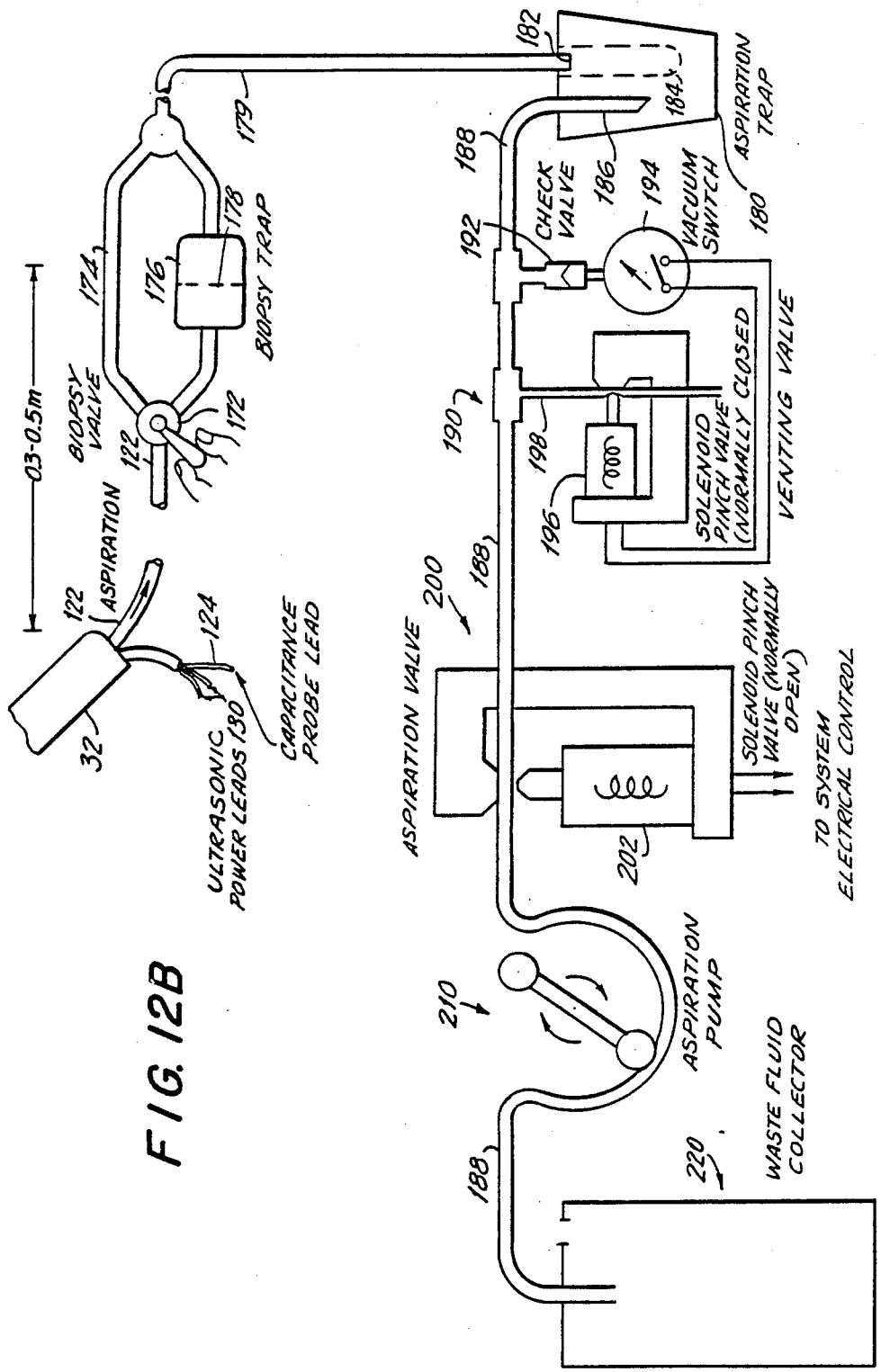
FIG. 12B shows schematically an aspiration system for use with the EUA.

FIG. 12 illustrates an overall endoscopic ultrasonic aspiration system. An irrigation fluid source 170 is located about 1-2 meters above the EUA. This distance provides sufficient hydrostatic pressure to keep the bladder neither distended nor collapsed.

Aspirated fluid and tissue passes through the aspiration hose 122 to a two-position biopsy valve 172. Ordinarily, the debris will be directed by the valve 172 through a direct hose 174 toward the source of suction. However, when the surgeon sees suspected tissue of which a biopsy would be desirable, the valve 172 can be thrown to direct the debris to a biopsy trap 176. The biopsy trap is a watertight vessel having a transverse screen 178 through which the aspirated debris must pass. The desired tissue can be rapidly collected on the screen and taken away for histological analysis. The biopsy trap should be relatively close to the EUA, for example about 0.3 to 0.5 meter. Because it is close, the hose 122 can clear very rapidly so that the biopsy material can be collected without unnecessary delay after the suspect tissue is spotted. The trap can also be kept sterile so that samples can be collected without contaminating either the sample itself or the surgeon's gloves.

The aspirated debris then passes through a line 179 to the main aspiration trap 180. The trap 180 is a closed vessel having an inlet 182 surrounded by a sock-shaped screen 184, which filters the debris. After filtration, tissue can be removed for medical examination in bulk. The trap has an outlet 186 away from the screen 184.

The screens 178 and 184 are not particularly fine. Their openings may advantageously be about 1 mm square so as to pass blood clots, etc., without clogging. On the other hand, the screen gauge is selected to trap pieces of tissue whose size is about the same as the inside diameter of the working tip 80, which is about the dimenson of the tissue that is cored out of the organ being resected.

After filtration, the debris passes through a line 188 to a venting valve 190. The valve 190 has a check valve 192, which opens and passes the pressure on the line 188 to a vacuum switch 194 if the pressure on the line 188 falls to a predetermined low level, which would indicate that the system is clogged. If the vacuum switch 194 opens, a solenoid 196 opens, and this opens a vent line 198, which vents the aspiration pressure to the atmosphere.

Overall control of aspiration pressure is provided by a main valve 200 operated by a solenoid 202.

Pumping is provided by a peristaltic pump 210. Waste aspiration fluid is received in a collecting vessel 220.

Figure 13:
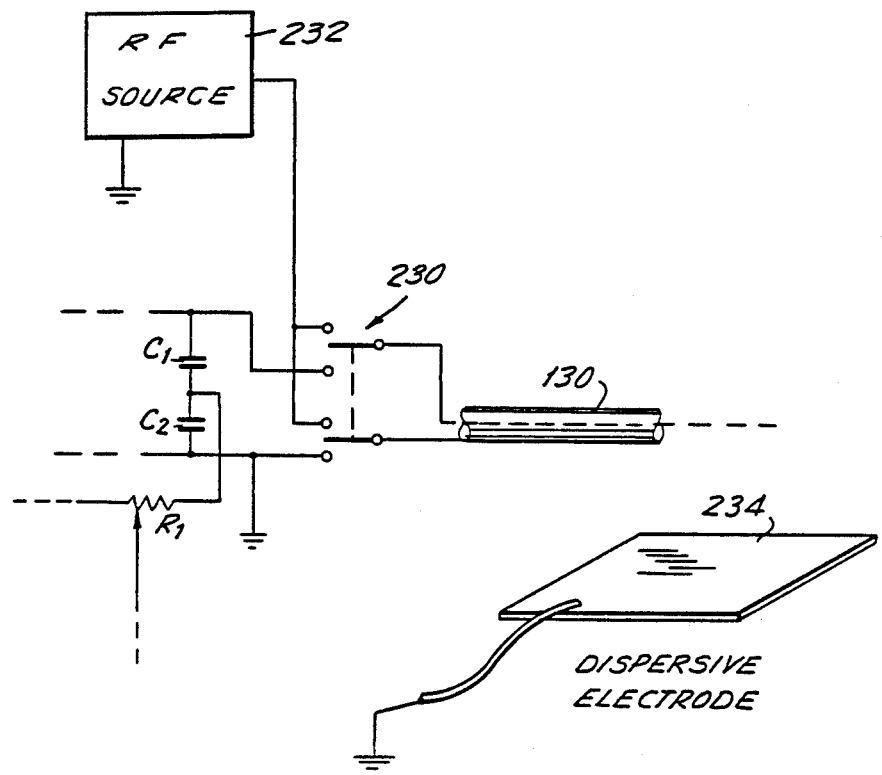
FIG. 13 is a schematic diagram of part of an alternate ultrasonic power supply for use with the EUA.
Figure 19:
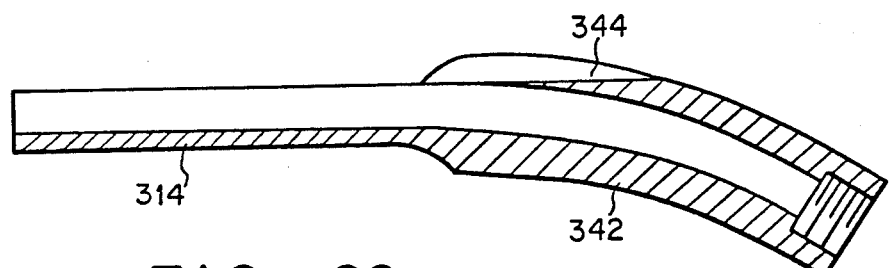
FIG. 19 is a view of the transformer input section of the invention.
Figure 20:
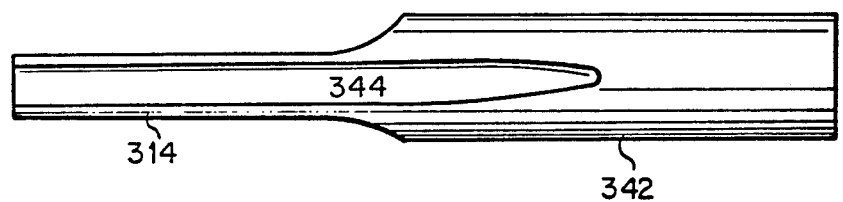
FIG. 20 is a view taken along line 20—20 of FIG. 19.

FIG. 13 shows elements of an alternate generator for driving the EUA in electro-cauterization of tissue. A double-pole, two-position switch 230 is provided for selecting the source of the signal to be applied to the transducer cable 130. In one position the switch selects the transducer drive signal across capacitors $C_1$, $C_2$ in the generator system, as discussed previously with reference to FIGS. 10A and 10B. In the other position the conductor and coaxial shield of the cable 130 are tied together and connected to a radio-frequency source 232. The RF signal is advantageously a pulsed RF current with a peak amplitude of 1500 volts. The waveform is a sharply decaying damped sinusoidal waveform with a frequency of about 500 kHz. The pulse repetition rate is about 20 kHz. To complete the circuit from the RF source to ground, a grounded dispersive electrode 234 is placed in contact with the skin of the patient. The surface area of contact should be as great as possible to prevent burns and shock effects. Thus, RF provided to the tip 80 passes through the patient to ground for endoscopic tissue cauterization.

The generator advantageously has the following operator controls: on/off foot switches for vibration, aspiration, and light; continuous/pulsed ultrasonic vibration mode; vibration amplitude; and optionally a switch 230 to connect the EUA to an RF source.

Referring to FIG. 14, the operational end of the open channel endoscopic ultrasonic aspirator generally designated 310, comprises a telescope 312 and resonator 314.

Telescope 312 is mounted within a hermetically sealed tube or upper lumen 316. Telescope 312 includes a cylindrical lens system (not shown) and at least one optical fiber (not shown) which transmits light from a light source to the operating site at the end of the telescope. Other illumination sources may be used. The cylindrical lens system allows the surgeon to view the operating site through an eyepiece at a point far removed from the operating site.

Resonator 314 is located within another hermetically sealed tube or lower lumen 318. Resonator 314 is a tube which is cut open from its working end at least to node 332 of aspirator 310. The significance of node 332 is discussed in detail below. Alternatively, resonator 314 may be cut open along its entire length. As a result, the cut portion of resonator 314 is in the form of a channel having a U shape in cross-section.

When the resonator 314 and lower lumen 318 are cut open along their entire length, the telescope 312 is suspended partially within this opening, and an aspirator of minimum size is achieved along its entire length. Casing 320, made of a rigid material, serves principally to maintain the telescope 312 in proper position over the cut portion of resonator 314 and lumen 318.

The opening of the operating tip of the resonator 314 does not affect its ultrasonic performance provided that at least half the tip remains. Dissection rates are unaffected since only the lower half of tip contacts tissue in normal usage and the tissue slivers removed by ultrasonic dissection using complete tubular tips are never the size of a full bore diameter.

In one embodiment, the resonator 314 is cut only to node 332. Thus, the operating portion of the aspirator is of smaller size than the opposite end which contains lumen 318. As shown in FIGS. 14–18, the tubular casing 20 surrounding the telescope 312 and resonator 314 is not round but is oval in shape to maintain the circumference of the EUA at the preferred minimum range. The oval casing provides accommodation of working implements within the smallest possible perimeter.

Upper lumen 316, in which telescope 312 is housed, fits into the opening at the end of resonator 314. Lower lumen 318, like resonator 314, is a tube which is cut open from its working end at least to node 332 of aspirator 310. Lower lumen 318 is fastened to upper lumen 316 by two beads of adhesive-sealant 326, such as an epoxy, so that upper lumen 316 fits into the opening of lower lumen 318 as shown in detail in FIG. 17b. Upper lumen 16 and lower lumen 318 can be made of any semi-rigid material; however, when upper and lower lumens 316 and 318 are made of an electrically insulating material, upper and lower lumens 316 and 318 electrically isolate resonator 314 from the remainder of the aspirator 310, the patient and the surgeon, so that an electrocauterizing current can be safely applied to the resonator 314.

Figure 22:
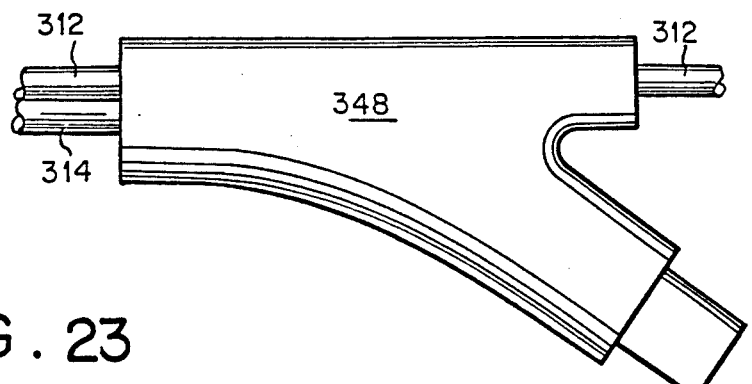
FIG. 22 is an illustration of the transformer input section with telescope inserted and which is further sealed with an elastomeric material.
Figure 23:
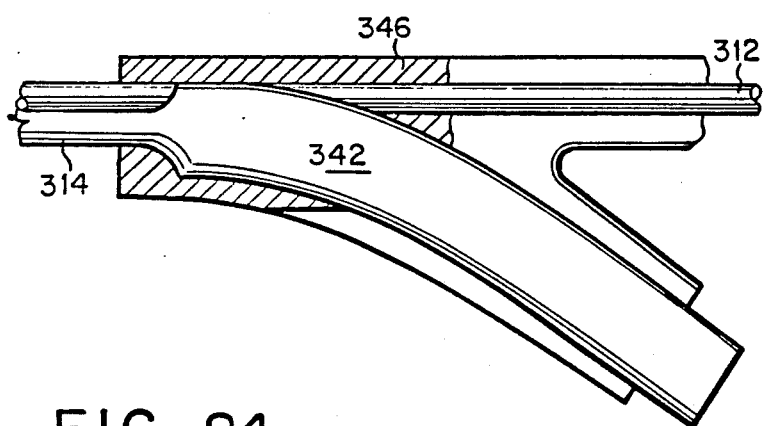
FIG. 23 is a view of FIG. 22 with a portion of the elastomeric sealing material removed.

In order to maintain the tip of resonator 314 adjacent to and in close proximity to upper lumen 316, plug 322 is inserted into lower lumen 318 between the lower surface of resonator 314 and the upper inner surface of lower lumen 318. Plug 322 is crescent shaped in cross-section so that its surfaces engage the lower surface of resonator 314 and the upper inner surface of lower lumen 318, and cause upper lumen 316 to be positioned within the opening of the U shaped tip of resonator 314 as shown in FIGS. 14 and 16. In addition to maintaining the position of the tip of resonator 314 adjacent to upper lumen 316, plug 322 also helps seal the cavity of the aspirator 310 between the lower surface of upper lumen 316 and lower lumen 318, leaving the aspiration channel 328 between resonator 314 and upper lumen 316 as the only opening into that cavity. As shown in FIGS. 22 and 23, a further seal 346 is located at the transformer input section, and this completely prevents the removed material from contacting the remaining parts of the aspirator.

Even without plug 322 in place, however, fluids would enter the channel at the point of tissue dissection. Since there is a very small clearance between the resonator 314 and upper lumen 316, flow is principally restricted to the end of the tip. The hydrodynamic resistance presented to flow below or outside of the channel is greater than the resistance of the open channel and therefore, substantially all flow will take place in the intended manner i.e., by suction through lower lumen 318.

Plug 322 is preferably made of a material that will yield when brought into contact with the ultrasonically vibrating tip of resonator 314. Illustratively, plug 322 is made of an epoxy or polyester resin, a thermoplastic or elastomeric material. By using such yielding materials, any mechanical interference between plug 322 and the ultrasonically vibrating tip of resonator 314 is minimized or removed completely by physical abrasion after the tip of resonator 314 has begun to vibrate. During operation, tissue aspiration proceeds in the same manner as if the tip were a closed tube. Furthermore, since the dissecting edge of the tip appears as a "U" to surgeons viewing this edge through the telescope 312, direct vision of the entire cutting surface is possible. Such a desirable view cannot be obtained using a closed tube aspirator tip.

Use of an electrocauterizing current may prove an advantageous adjunctive procedure in endoscopic ultrasonic surgery. In electrocauterization, a metal tip, loop or other surgical probe is connected to source of high voltage radio frequency current generated by a spark gap oscillator or a generator that produces the same pulsating flow of electrical current that is characteristic of such oscillators. When the probe is brought into contact with tissue, this current flows through the tissue from the point of contact to a large collecting electrode placed under the patient and in direct contact with the skin.

When the ultrasonic tip is effectively insulated from the telescope and sheath, it is possible to not only apply the electrocauterizing potential directly to the tip, but also, if an insulated transducer is employed to vibrate the tip, to simultaneously apply both ultrasonic vibration and electrocauterization in an endoscopic instrument for the purpose of dissecting and cauterizing at the same time, and thereby reducing the surgical operating time.

Upper lumen 316 and lower lumen 318 are hermetically sealed within semi-rigid tubular casing 320. Due to the shape of upper and lower lumens 316 and 318 and the way in which they are attached to one another, a pair of irrigation fluid channels 324 are formed when upper and lower lumens 316 and 318 are mounted within casing 320, as shown in FIGS. 14 and 16.

As discussed above, resonator 314 has a U shaped cross-section at its operational end, but, according to a preferred embodiment, assumes a closed-off tubular shape at node 332. A cross-sectional drawing of the aspriator at node 332 is shown in FIG. 17. At node 332 both resonator 314 and lower lumen 318 are tubular in shape and aspiration channel 328 is circular in cross-section. Since resonator 314 does not vibrate at node 332, resonator 314 can contact the inner surface of lower lumen 318 without adversely affecting the vibration of aspriator 314 at its operational end. However, since resonator 314 vibrates throughout its length except at node 332, the remainder of resonator 314 between node 332 and the transducer which causes resonator 314 to vibrate, should not contact the inner surface of lower lumen 18. Therefore, as shown in FIGS. 15 and 18, there is a space 30 between lower lumen 318 and resonator 314 in the aspirator between node 332 and the transducer.

In operation, after the aspirator of the present invention has been partially inserted into a patient's body so that the operational end of the aspirator is positioned adjacent to the tissue that is to be removed by the aspirator, resonator 314 is caused to vibrate at an ultrasonic frequency by a transducer. When resonator 314 vibrates at its ultrasonic frequency, vibration of the tip of resonator 314 allows the tip to cut through tissue. In order to remove the cut tissue from the patient's body, irrigation fluid is pumped through irrigation fluid channels 324 of the aspirator to the operation site. The irrigation fluid is removed from the operation site by suction that is applied to aspiration channel 328 of resonator 314.

Because the end of resonator 314 near its operational end has a U shape in cross-section, irrigation fluid can enter aspriator channel 324 along the entire cut open section of resonator 314 within lower lumen 318, thereby reducing the amount of suction at any point along the cut open section. However, since the end section of lower lumen 328 is sealed by plug 322, leaving only the U shaped opening of aspiration channel, suction is maintained within lower lumen 318 so that there is sufficient suction at the U-shaped tip of resonator 314.

Although the most preferred resonator shape is a half circle or U shape in cross section, other shapes can be used. For example, a V-shape or an open rectangular or square shape having straight, angled, or rounded corners is also acceptable. The provision of any of these shapes for a channel type (i.e., a base portion with two side portions and an open top) member is within the scope of this invention. Also, plug 322 would be designed to match the configuration of the resonator tip.

When the optimum minimal size of the aspirator is desired, the cut resonator 314 and lower lumen 18 should extend throughout the entire length of the aspirator. This embodiment of the invention is shown in FIGS. 19–24. Since telescope 312 would be located partially within resonator 314 and lower lumen 318, thus providing an arrangement for the instrument which would be similar in cross section to FIG. 16 but extending throughout the entire length of the aspirator. The resonator is anchored at node 332 by seal 340. This seal which can be cast from rubber or other elastomeric material, would also prevent fluids from seeping in the space between resonator 314 and lower lumen 318.

Figure 21:
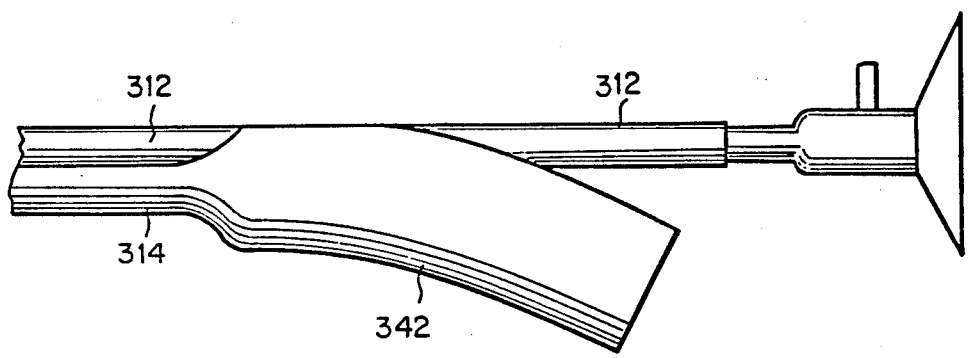
FIG. 21 is a view of the transformer input of the invention when the telescope is inserted.

FIGS. 19–24 show the arrangement of telescope 312 and resonator 314 in the area of the transformer input section 342. As shown best in FIG. 20, a groove 344 is cut in the top of the transformer input section 342 to provide space for the telescope 312. The telescope 312 is inserted in groove 344 as shown in FIG. 21. This groove 344 in transformer input section 342 along with the open channel shape of resonator 314 enables telescope 312 to be fitted partially therein so as to minimize the outer diameter or French size of the overall aspiration unit.

In this embodiment, the open channel resonator requires at some point a mechanism for connecting the open channel to a closed tube or passage for removal of biological material and fluid from the aspirator to a waste container, collection vessel, or trap. The transformer input section 342, illustrated in FIGS. 19–23, is bent at a predetermined angle to provide space for the telescope 312. The resonator channel 314 and the telescope 312 also separate at this point. To prevent fluid and biological tissue from flowing back to the telescope 312 or to the handpiece, a castable elastomeric or thermoplastic material is utilized to seal this area.

Figure 24:
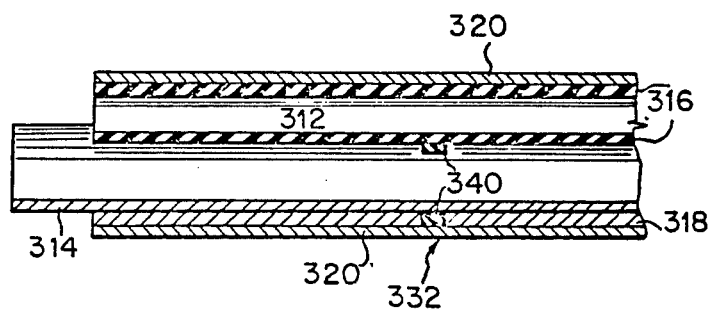
FIG. 24 is a cross sectional view similar to FIG. 15, but illustrating an alternate embodiment of the invention.

FIGS. 23 and 24 illustrate this sealing material 346 and outer sheath 348 for this area of the aspirator. This sealing material 346, generally comprising a elastomeric or thermoplastic self-curing material of relatively low hardness or durometer (i.e., less than 80 Shore A) is essential for preventing the fluid which is desired to be removed through the lower lumen 318 from contaminating or seeping into the handpiece of the aspiration unit. During the manufacture of the aspirator, after the telescope 312 is placed within the resonator channel 314, sheath 348 is placed round the joint area and the synthetic elastomeric or thermoplastic material is cast there between. Preferably, this cast material is a synthetic rubber having a durometer hardness of approximately 40 Shore A. Surprisingly, while high friction losses would be expected for such an arrangement, the losses which are actually encountered are very small, because the actual frequency and vibrational velocities are very low in the encapsulated area. Therefore, isolation of the handpiece of the unit from the fluids removed from the body of the patient is achieved without reducing the vibrational forces that are transmitted to the working tip of the aspirator. The seal 346 also isolates the unit from the atmosphere.

Referring now to FIG. 24, it is evident that seal 340 prevents the fluids which are to be removed from the patient from flowing beneath or outside of resonator 314, such as between resonator 14 and the lower lumen 318. However, this seal 340 does not obviate the need for the cast sealing material 346, since the cast sealing material is used to prevent the fluid, which is in lower lumen 318 from contaminating the handpiece of the overall aspiration unit.

Figure 25:
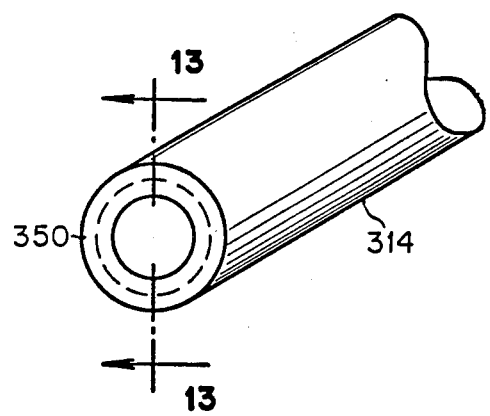
FIGS. 25, 26 and 27 are detailed views of resonator tip modifications for the invention.
Figure 26:
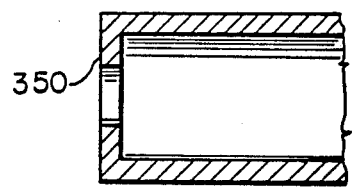
Figure 27:
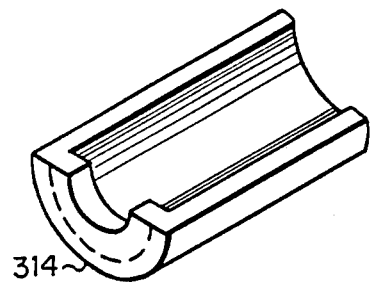

Referring now to FIGS. 25–27, there are illustrated various additional modified working tip arrangements and configurations for the resonator 314 of the invention. As shown in FIG. 27, the working tip can be of a partially blocked off channel which provides advantages with respect to precision cutting of the biological material. This same effect can be achieved by narrowing the channel means by tapering the tip or by reducing the cross sectional area of other configurations, i.e., such as by gradually diminishing the cross sectional area or size of the channel means or by otherwise configuring the open area of working tip to be of a smaller dimension than of the resonator 314.

In other embodiments, as shown by FIGS. 25 and 27, the tip may comprise part of the tubular unit which is also reduced or restricted in diameter at the working point. The end of the tube can be restricted by means of an overlap 350 or by way of a crimping on the end of the tube to restrict the outer diamter at the working point. This tubular design provides an advantage wherein blockage of the resonator tube 314 is prohibited, since any removed biological material must pass through the smaller bore of the open tip to enter the tube 314. Thus, the material removed would not be able to block or clog the tube 14 when suction is used to withdraw such removed biological material.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method of removing cellular material from a compliant tissue relatively deep within a biological body through a narrow orifice comprising:
    providing an elongated surgical instrument which comprises an elongated working end having a length of at least about 8 cm, a circumference of no more than about 29 mm, and a working tip at the forward end thereof, said instrument including means for viewing said working tip and said material to be removed;
    inserting said forward end of said elongated surgical instrument into the orifice with said working tip located close to the material to be removed; and
    vibrating said working tip longitudinally at a frequency of about 10–20 kHz so as to cavitate the intracellular fluids in such material to destroy the cells thereof while monitoring the removal of said material through the viewing means of said instrument.

2. The method of claim 1, including vibrating said working tip with a longitudinal stroke of at least about 350 microns.

3. The method of claim 2, wherein such longitudinal stroke is at least about 700 microns.

4. The method of claim 1, including vibrating said working tip with a maximum velocity of at least about 1000 cm/sec.

5. The method of claim 4, wherein said maximum velocity is at least about 2000 cm/sec.

6. The method of claim 1, including employing a blunt working tip.

7. The method of claim 1 which further comprises providing the working tip with open channel means to facilitate the removal of said material.

8. The method of claim 7 which further comprises selecting an open channel means which tapers and diminishes along its length.

9. The method of claim 7 which further comprises selecting an open channel means which comprises a base portion and two side portions.

10. The method of claim 7 which further comprises selecting an open channel means which has a cross-sectional area in the shape of a U or V.

11. The method of claim 7 which further comprises selecting an open channel means of substantially uniform cross-section.

12. The method of claim 7 which further comprises selecting an open channel means which further includes tip means of smaller cross-section than the open channel means.

13. The method of claim 1 which further comprises providing said instrument with a radio-frequency source so that said working tip can receive a RF current for cauterization of said tissue when said tip is not vibrating.

14. The method of claim 13 which further comprises providing said instrument with means for selecting the source of signal to be provided to said working tip from one of said radio frequency source or a source for generating ultrasonic vibrations.

15. The method of claim 14 which further comprises providing said instrument with a switch as the selecting means.

16. A method of removing cellular material from a compliant tissue at an operating site at least about 8 cm deep within a biological body through a narrow orifice comprising:
    providing an elongated surgical instrument which comprises an elongated working end having a length of at least about 8 cm, a circumference of no more than about 29 mm, and a working tip at the forward end thereof, said instrument including means for viewing said working tip and said material to be removed;
    inserting said elongated surgical instrument at least about 8 cm deep into said body through the orifice with said working tip being located close to the material to be removed; and
    vibrating said working tip longitudinally at a frequency of about 10–20 kHz so as to produce pressure waves to disintegrate such material while monitoring the removal of said material through the viewing means of said instrument.

17. The method of claim 16, including vibrating said working tip with a longitudinal stroke of at least about 350 microns.

18. The method of claim 17, wherein such longitudinal stroke is at least about 700 microns.

19. The method of claim 16, including vibrating said working tip with a maximum velocity of at least about 1000 cm/sec.

20. The method of claim 19, wherein such maximum velocity is at least about 2000 cm/sec.

21. The method of claim 20, including cavitating the intracellular fluids in such material to destroy the cells thereof.

22. The method of claim 21 including employing a blunt working tip.

23. The method of claim 22, including inserting said narrow elongated surgical instrument at least about 19 cm into said body.

24. The method of claim 16 which further comprises providing said instrument with a radio-frequency source so that said working tip can receive a RF current for cauterization of said tissue when said tip is not vibrating.

25. The method of claim 24 which further comprises providing said instrument with means for selecting the source of signal to be provided to said working tip from one of said radio frequency source or a source for generating ultrasonic vibrations.

26. The method of claim 25 which further comprises providing said instrument with a switch as the selecting means.

27. A method of removing cellular material from a compliant tissue at an operating site at least about 8 cm deep within a biological body through an orifice no more than about 29 mm in circumference comprising:
providing a surgical instrument having an elongated sheath at least about 8 cm in length and no more than about 29 mm in circumference, the sheath having a hollow bore therethrough,
locating an elongated probe spaced within the hollow bore of the sheath, with a working end of the probe projecting beyond the end of the sheath, the probe having a hollow bore therethrough, thereby forming a first fluid passage in the space between the probe and the sheath, and a second fluid passage within the probe,
inserting the sheath into such body orifice with the working end of the probe being at such operating site and close to such material to be removed,
introducing a fluid into one of the two fluid passages to irrigate such operating site,
vibrating the probe longitudinally at a frequency of about 10–20 kHz so as to produce pressure waves sufficient to disintegrate the cells of such material to be removed, said instrument including means for viewing said working tip and said material to be removed, and
applying suction to the other of the fluid passages to withdraw such fluid and such matter to be removed from such operating sire while monitoring the removal of said material through the viewing means of said instrument.

28. The method of claim 27, including providing a surgical instrument no more than about 25 mm in circumference.

29. The method of claim 27, including providing a surgical instrument at least about 19 cm in length.

30. The method of claim 29, including providing a surgical instrument no more than about 25 mm in circumference.

31. A method for removing cellular material from a compliant tissue within a biological body through a natural or surgically created orifice comprising:
inserting into said orifice an aspirator comprising:
handpiece means;
elongated sheath means extending from said handpiece means and having a hollow bore therethrough;
unitary vibration generating means having a first portion which is mounted in said handpiece means, a second portion which is located in the hollow bore of said sheath, and a third portion comprising a resonator tip which extends beyondthe end of said sheath for generating vibrations having an amplitude sufficient to disintegrate said cellular material at a work site in the body of the patient;
means for irrigating said work site with fluid to assist in the removal of disintegrated cellular material;
aspiration means for removing said disintegrated cellular material from said work site; and
means for viewing said work site from said handpiece
so as to position said resonator tip of said aspirator in close proximity to the cellular material to be removed;
vibrating said resonator tip of said aspirator to cavitate the intracellular fluids of the cellular material to destroy the cells thereof; and
removing the destroyed cellular material through said aspiration means of said aspirator.

32. The method of claim 31 which further comprises providing the aspirator with a radio-frequency source so that the resonator tip can receive RF current for cauterizing tissue at the work site when said tip is not vibrating.

33. The method of claim 32 which further comprises providing the aspirator with a switch for selectively connecting one of said radio-frequency source or said vibration generating system to said tip.

34. A method for removing cellular material from a compliant tissue within a biological body through a natural or surgically created orifice comprising:
inserting into said orifice an aspirator comprising:
a hollow handpiece;
an elongated sheath having a hollow bore communicating with the interior of the handpiece and having a working end away from the handpiece;
a vibration source within the handpiece for producing mechanical vibrations in response to an alternating current supplied to said vibration source;
means for supplying such alternating current to said vibration source;
elongated tool means coupled to the vibration source and passing through said hollow bore of the sheath to a work site beyond the working end of the sheath for transmitting such mechanical vibrations to the work site, said tool means including working tip means for contact with the work site;
viewing means extending from the handpiece to the work site for providing a view from the handpiece of the work site;
means for supplying fluid to said work site through a fluid space defined between said tool means and said hollow bore of said sheath;
fluid detection means for detecting the presence of fluid in the fluid space and connected to the means for supplying alternating current for terminating such supplied alternating current and thereby stopping such mechanical vibrations when such fluid is not present, and
means for removing said fluid from said work site through conduit means, the end of said conduit means nearest the work site formed by said working tip means
so as to position said working tip means of said aspirator in close proximity to the cellular material to be removed;
vibrating said working tip means of said aspirator to cavitate the intracellular fluids of the cellular material to destroy the cells thereof; and removing the destroyed cellular material through said fluid removal means of said aspirator.

35. The method of claim 34 which further comprises providing the aspirator with a radio-frequency source so that the elongated tool means can receive RF current for cauterizing tissue at the work site when said tool means is not vibrating.

36. The method of claim 35 which further comprises providing the aspirator with a switch for selectively connecting one of said radio-frequency source or said vibration generating system to said elongated tool means.

37. A method for removing cellular material from a compliant tissue within a biological body through a natural or surgically created orifice comprising:
  inserting into said orifice an apparatus comprising:
    a handpiece;
    an elongated sheath extending from the handpiece and having a hollow bore therethrough;
    high frequency vibration source means mounted in the handpiece for generating a first amplitude;
    first velocity transformer means located in the hollow bore within the sheath and spaced therefrom, having an input end and an output end, the input end being coupled to the vibration source to be vibrated thereby, and the output end vibrating in response to such received vibrations with a second amplitude greater than such first amplitude;
    second velocity transformer means having an input end and an output end, the input end being coupled to the output end of the first transformer to be vibrated thereby, and the output end vibrating in response to such received vibrations with a third amplitude greater than such second amplitude, said third amplitude being sufficient to disintegrate said cellular material, said second velocity transformer means having working tip means extending beyond the end of the sheath away from the handpiece for contacting said cellular material, said working tip means having a smaller cross-sectional area than that of said second velocity transformer means;
    the second transformer means when vibrating, having a substantially constant mechanical stress level in substantially all of its length, the output end of the first transformer velocity means and the second velocity transformer means forming a unitary component to minimize the production of transverse flexural vibrations;
    said high-frequency vibration source means and said first and second velocity transformer means being elongated and having a continuous hollow bore extending along a common longitudinal axis thereof, thereby forming first fluid passage means in a space defined between the first and second velocity transformer means and the sheath, and second fluid passage means along said common longitudinal axis;
    means for introducing fluid into one of said fluid passage means to irrigate an operating site adjacent said working tip means of the second velocity transformer means where said cellular material is contacted and disintegrated; and
    means for applying suction to the other of said fluid passage means to remove such fluid and such disintegrated cellular material from such operating site so as to position said working tip means of said apparatus in close proximity to the cellular material to be removed;
vibrating said working tip means of said apparatus to cavitate the intracellular fluids of the cellular material to destroy the cells thereof; and
removing the destroyed cellular material through said other fluid passage of said apparatus.

38. The method of claim 34 which further comprises providing the aspirator with a radio-frequency source so that the working tip means can receive RF current for cauterizing tissue at the work site when said tip is not vibrating.

39. The method of claim 38 which further comprises providing the aspirator with a switch for selectively connecting one of said radio-frequency source or said vibration generating system to said working tip means.

40. A method for removing cellular material from a compliant tissue within a biological body through a natural or surgically created orifice comprising:
  inserting into said orifice an aspirator comprising:
    a hollow handpiece;
    an elongated sheath having a hollow bore communicating with the interior of the handpiece and having a working end away from the handpiece;
    a vibration source within the handpiece for producing mechanical vibrations in response to an alternating current supplied to said vibration source;
    means for supplying such alternating current to said vibration source;
    elongated tool means coupled to the vibration source and passing through a hollow bore of the sheath to a work site beyond the working end of the sheath for transmitting such mechanical vibrations to such work site;
    viewing means extending from the handpiece to such work site for providing a view from the handpiece of such work site;
    means for supplying fluid to a fluid space defined between said tool means and said hollow bore of said sheath; and
    fluid detection means for detecting the presence of fluid in the fluid space and connected to the means for supplying alternating current for terminating such supplied alternating current and thereby stopping such mechanical vibrations when such fluid is not present
  so as to position said elongated tool means of said apparatus in close proximity to the cellular material to be removed;
  vibrating said elongated tool means of said aspirator to cavitate the intracellular fluids of the cellular material to destroy the cells thereof; and
  removing the destroyed cellular material.

41. The method of claim 40 which further comprises providing the aspirator with a radio-frequency source so that the elongated tool means can receive RF current for cauterizing tissue at the work site when said tool means is not vibrating.

42. The method of claim 41 which further comprises providing the aspirator with a switch for selectively connecting one of said radio-frequency source or said vibration generating system to said tool means.

43. A method for removing cellular material from a compliant tissue within a biological body through a natural or surgically created orifice comprising:
  inserting into said orifice an apparatus comprising:

a handpiece;

an elongated sheath extending from the handpiece and having a hollow bore therethrough;

vibration means comprising:

high-frequency vibration source means mounted in the handpiece for vibrating with a selected wavelength and with a first amplitude;

first velocity transformer means located in the hollow bore within the sheath and spaced therefrom for amplifying vibrations from the vibration source means and having an input section and an output section, the input section being unitary with the vibration source means and the output section being smaller in cross-sectional area than the input section, and second velocity transformer means having an input end and an output end, the input end being unitary with the output section of the first velocity transformer means for amplifying vibrations thereof to a sufficient velocity to disintegrate said cellular material and to minimize the production of transverse flexural vibrations, the output end vibrating in response to such received vibrational energy for further transmitting such vibrational energy;

said second velocity transformer means having a working tip extending beyond the end of the sheath away from the handpiece;

said high-frequency vibration source means and each of said velocity transformer means being elongated and each having a continuous hollow bore extending along a common longitudinal axis thereof, thereby forming; first fluid passage means in a space defined between the first and second velocity transformer means and the sheath, and second fluid passage means along said common longitudinal axis;

means for introducing fluid into one of said fluid passage means to irrigate an operating site adjacent the working tip of the second velocity transformer means where said cellular material is disintegrated, and means for applying suction to the other of said fluid passage means to remove said fluid and disintegrated cellular material from such operating site so as to position said working tip of said apparatus in close proximity to the cellular material to be removed;

vibrating said working tip of said apparatus to cavitate the intracellular fluids of the cellular mateerial to destroy the cells thereof; and removing the destroyed cellular material.

44. The method of claim 43 which further comprises providing the aspirator with a radio-frequency source so that the working tip can receive RF current for cauterizing tissue at the work site when said tip is not vibrating.

45. The method of claim 44 which further comprises providing the aspirator with a switch for selectively connecting one of said radio-frequency source or said vibration generating system to said tip.

46. A method for removing cellular material from a compliant tissue within a biological body through a natural or surgically created orifice comprising:

inserting into said orifice an aspirator comprising:

a hollow handpiece;

an elongated sheath having a hollow bore communicating with the interior of the handpiece and having a working end away from the handpiece;

high-frequency vibration source means mounted in the handpiece comprising transducer means for generating high-frequency vibrations of a selected wavelength and having a first amplitude and vibration amplifying means for receiving the vibrations generated by the transducer means and amplifying said vibrations to ultrasonic vibrations of a frequency of between 10 and 20 KHz, said vibration amplifying means comprising:

first velocity transformer means of an elongated member having an input end and an output end for amplifying vibrations from said vibration source means the input end being coupled to the transducer means and the output end vibrating in response to such received vibrations with a second amplitude greater than said first amplitude, and second velocity transformer means of an elongated member having an input end and an output end for amplifying vibrations from the first velocity transformer means, the input end being unitary with the output end of the first velocity transformer means to be vibrated thereby and to minimize the production of transverse flexural vibrations, the output end vibrating in response to such received vibrations with the desired frequency while further having a substantially constant mechanical stress level in substantially all its length;

elongated tool means coupled to the output end of said second velocity transformer means and passing through the hollow bore of the sheath to a work site beyond the working end of the sheath for transmitting the amplified vibrations to said work site for disintegration of said cellular material thereof;

means for aspirating said disintegrated cellular material portion from the work site; and viewing means extending from said handpiece to said work site for providing a view from the handpiece of said work site so as to position said elongated tool means of said aspirator in close proximity to the cellular material to be removed;

vibrating said elongated tool means of said aspirator to cavitate the intracellular fluids of the cellular material to destroy the cells thereof; and removing the destroyed cellular material.

47. The method of claim 46 which further comprises providing the aspirator with a radio-frequency source so that the elongated tool means can receive RF current for cauterizing tissue at the work site when said tool means is not vibrating.

48. The method of claim 47 which further comprises providing the aspirator with a switch for selectively connecting one of said radio-frequency source or said vibration generating system to said tool means.

* * * * *